(12) United States Patent
Ho et al.

(10) Patent No.: US 9,201,052 B2
(45) Date of Patent: Dec. 1, 2015

(54) ANALYSIS APPARATUS AND METHOD

(75) Inventors: Louise Ho, Nelson (NZ); Yaochun Shen, Cambridge (GB); Phillip F. Taday, Cambridge (GB); Thomas Rades, Dunedin (NZ)

(73) Assignee: TeraView Limited, Cambridge (GB)

( * ) Notice: Subject to any disclaimer, the term of this patent is extended or adjusted under 35 U.S.C. 154(b) by 1273 days.

(21) Appl. No.: 12/525,053

(22) PCT Filed: Jan. 29, 2008

(86) PCT No.: PCT/GB2008/000293
§ 371 (c)(1),
(2), (4) Date: Feb. 26, 2010

(87) PCT Pub. No.: WO2008/093067
PCT Pub. Date: Aug. 7, 2008

(65) Prior Publication Data
US 2010/0148070 A1 Jun. 17, 2010

(30) Foreign Application Priority Data

Jan. 29, 2007 (GB) .................................. 0701646.2
Jun. 26, 2007 (GB) .................................. 0712397.9

(51) Int. Cl.
*G01J 5/02* (2006.01)
*G01N 33/15* (2006.01)
*G01N 21/3581* (2014.01)
(Continued)

(52) U.S. Cl.
CPC ............ *G01N 33/15* (2013.01); *G01N 21/3563* (2013.01); *G01N 21/3581* (2013.01); *G01N 21/9508* (2013.01)

(58) Field of Classification Search
CPC .......... G01N 21/3581; G01N 21/9508; G01N 21/3563; G01N 33/15
USPC ............................ 250/341.8, 336, 336.1, 234
See application file for complete search history.

(56) References Cited

U.S. PATENT DOCUMENTS 5,679,954 A    10/1997  Soloman
7,728,296 B2 *  6/2010  Cole et al. .................. 250/338.1
(Continued)

FOREIGN PATENT DOCUMENTS

EP    0 864 857 A1    9/1998
EP    1 607 736 A1   12/2005
(Continued)

OTHER PUBLICATIONS

Authors: Phillip F. Taday and Thomas Rades, Title: Terahertz Pulsed Imaging—A Novel Tool for the Characterisation of Controlled Release Dosage Forms, Date: 2006, Publisher: Controlled Release Society, newsletter, vol. 23, No. 2.*
(Continued)

*Primary Examiner* — David J Makiya
*Assistant Examiner* — Taeho Jo
(74) *Attorney, Agent, or Firm* — Dickstein Shapiro LLP

(57) ABSTRACT

A method of performing dissolution analysis on a tablet, the method comprising: irradiating a tablet with radiation having at least one frequency in the range from 40 GHz to 100 THz; detecting radiation which has been transmitted through or reflected by the tablet; determining a parameter from the detected radiation indicative of the density of a coating layer of the tablet; and determining information about the dissolution characteristics of the tablet from said parameter.

25 Claims, 28 Drawing Sheets

(51) Int. Cl.
*G01N 21/95* (2006.01)
*G01N 21/3563* (2014.01)

(56) References Cited

U.S. PATENT DOCUMENTS

| | | | |
|---|---|---|---|
| 2003/0092595 A1* | 5/2003 | Romero et al. | 510/447 |
| 2005/0009728 A1 | 1/2005 | Smith et al. | |
| 2006/0235621 A1* | 10/2006 | Cole et al. | 702/19 |
| 2006/0255277 A1* | 11/2006 | Cole et al. | 250/341.1 |
| 2006/0280790 A1* | 12/2006 | Ju et al. | 424/464 |
| 2007/0138392 A1* | 6/2007 | Cole | 250/341.1 |
| 2007/0181811 A1* | 8/2007 | Mitrofanov | 250/341.1 |
| 2007/0190129 A1* | 8/2007 | Ahmed et al. | 424/451 |
| 2007/0257216 A1* | 11/2007 | Withers et al. | 250/580 |

FOREIGN PATENT DOCUMENTS

| | | |
|---|---|---|
| GB | 2 372 929 A | 9/2002 |
| GB | 2 380 920 A | 4/2003 |
| GB | 2 385 415 A | 8/2003 |
| GB | 2 405 466 A | 3/2005 |
| GB | 2 416 204 A | 1/2006 |
| WO | WO 96/15428 A1 | 5/1996 |
| WO | WO 03/078983 A1 | 9/2003 |
| WO | WO 2004/027398 A1 | 4/2004 |
| WO | WO 2004/106905 A1 | 12/2004 |
| WO | WO 2006/083001 A1 | 8/2006 |
| WO | WO 2006/092557 A1 | 9/2006 |

OTHER PUBLICATIONS

Authors: Paulo Costa, Jose Manuel Sousa Lobo, Title: Modeling and comparison of dissolution profiles, Date: 2001, Publisher: European Journal of Pharmaceutical Sciences.*

Authors: Anthony J. Fitzgerald, Bryan E. Cole, Philip F. Taday, Title: Nondestructive Analysis of Tablet Coating Thicknesses Using Terahertz Pulsed Imaging, Date: 2005, Publisher: Journal of Pharmaceutical Sciences, vol. 94, 177-183.*

Freita, et al, "Predication of Drug Dissolution Profiles From Tablets Using NIR diffuse reflectance spectroscopy: A Rapid and Nondestructive Method," *Journal of Pharmaceutical and Biomedical Analysis*, vol. 39, No. 1-2, pp. 17-21, Sep. 1, 2005.

* cited by examiner (a)

(b)

ANALYSIS APPARATUS AND METHOD

The present invention relates to the field of investigating and imaging pharmaceutical tablets using terahertz radiation. More specifically, the present invention relates to the field of investigating and imaging such tablets using pulsed terahertz radiation.

Terahertz technology allows for the first non-destructive imaging of chemical and/or structural features of the pharmaceutical tablet containing the active pharmaceutical ingredient (API) and excipients (fillers).

The structural and chemical features of the coatings and core of a tablet or other dosage form are frequently critically dependent upon the parameters used in designing and manufacturing the tablet. However, with existing analysis techniques, it is virtually impossible to be able to distinguish between tablets of nominally identical chemical ingredients or constituents but which have been fabricated using different process parameters without destroying the tablet.

The bio availability (rate of absorption of a drug by the body and therapeutic efficacy of the accompanying dosage form) of pharmaceutical products is commonly assessed by dissolution studies. Current dissolution studies involve dissolving tablets or other dosage forms in a bath and using high performance liquid chromatography (HPLC) or related techniques to study how the tablet dissolves. This technique has two main disadvantages. It is time consuming and also the tablet must be destroyed in order to perform the test.

By using terahertz analysis, the time to perform a dissolution study can be reduced to the time it takes to image a sample using terahertz radiation. Further, this technique is completely non-destructive which allows for direct measurement of tablets which can then be distributed. In other words, THz analysis provides a method of screening many tablets directly before use in clinical trails or on the market to determine their dissolution profiles. The ability to predict a dissolution profile using a non destructive Terahertz image leads to a variety of advantages including design & maintenance of in-spec product performance to avoid non compliance, accelerate development and improve product quality This method also opens up new methods for ensuring and protecting patient safety as well as the proprietary nature of dosage forms, including: inclusion of THz images within new drug applications to the US Food and Drug Administration and equivalent regulatory agencies in other countries, thereby adding a stage to help guarantee the efficacy of drugs and securing ownership or proprietary coverage of a dosage form based on a Terahertz image of the dosage form which is correlated to known and favourable dissolution properties.

The inventors have discovered that the density of the tablet coating is important to the dissolution characteristics.

In a first aspect the present invention provides a method of performing dissolution analysis on a tablet, the method comprising:
  irradiating a tablet with radiation having at least one frequency in the range from 40 GHz to 100 THz;
  detecting radiation which has been transmitted through or reflected by the tablet;
  determining a parameter from the detected radiation indicative of the density of a coating layer of the tablet; and
  determining information about the dissolution characteristics of the tablet from said parameter.

The radiation may be pulsed or CW radiation. In all aspects of the present invention preferably the THz radiation is in the range from 40 GHz to 10 THz, more preferably from 50 GHz to 5 THz.

One parameter which is indicative of the density is the thickness of the tablet coating. The tablet coating thickness may be derived from the time of flight of the radiation through the tablet coating. An accurate value for the tablet coating thickness can be derived by using the refractive index to convert the time of flight of the radiation through the tablet coating to a thickness value. The refractive index may be measured from the peak height of reflected THz radiation.

The weight of the tablet coating may also be measured in order to determine the density from the thickness of the tablet coating. It should be noted that the weight on its own is not a reliable indicator of dissolution. However, it has been found that tablet thickness on its own and time of flight of radiation on their own are reliable indicators of correlation since a thicker tablet coating reliably indicates lower density and hence faster dissolution. Thus, it is possible to just measure time of flight of radiation or the thickness to compare dissolution characteristics between different tablets which should be chemically identical.

The tablet thickness is not the only indicator of density. The refractive index varies with density. The refractive index may be determined in many ways. One possible way is from the maximum signal strength of the radiation reflected by the table. Typically the Terahertz electric field peak strength (TEFPS) will be used as the signal strength Thus, the size of the reflected signal from the external surface of the tablet may be measured to indicate the refractive index and hence the density of the coating. The size of the reflected signal may be divided by the size of the reflected signal from a perfect reflector such as a mirror. The signal may also be measured which is due to the reflection from the interface between the coating and the core of the tablet to give density information about the coating. This may be expressed as an interface index where the signal reflected from the interface between the coating and the core is divided by the size of the signal reflected from the external surface of the tablet.

In a second aspect, the present invention provides a method of performing dissolution analysis on a tablet, the method comprising:
  irradiating a tablet with radiation having at least one frequency in the range from 40 GHz to 100 THz;
  detecting radiation which has been reflected by the tablet;
  determining a parameter from the detected radiation indicative of maximum signal strength reflected by the tablet; and
  determining information about the dissolution characteristics of the tablet from said parameter.

Information about the dissolution characteristics is determined by using a positive correlation between the density and the time which dissolution takes. If the tablet coating thickness or time of flight is measured, the correlation will be negative since these parameters suggest a lower density coating.

The dissolution characteristics may be defined by dissolution parameters selected from: the mean dissolution time; the dissolution rate constant and the dissolution at specified times.

The parameter may be measured for a plurality of points on said tablet. The parameter may be measured at a single point or even an image may be obtained. The parameter may be measured on the two main opposing surfaces of the tablet and the central band to give information about the density of the coating over the whole of the tablet. The inventors have found that the central band is often the weak part of the tablet, hence it is preferable to measure the signal from the central band either on its own or in combination with measurements from other points of the tablet.

In a preferred embodiment the tablet is a sustained release tablet.

The present invention may be used for quality control, thus in a third aspect, the present invention provides a method of determining if a tablet is of sufficient quality, said method comprising:

irradiating a tablet with radiation having at least one frequency in the range from 40 GHz to 100 THz;

detecting radiation which has been transmitted through or reflected by the tablet;

determining a parameter from the detected radiation indicative of the density of a coating layer of the tablet; and determining if said tablet is of sufficient quality by comparing the parameter of the tablet with a pre-determined reference value and rejecting said tablet the density of the coating layer is lower than said reference value.

In a fourth aspect, the present invention provides an apparatus for performing dissolution analysis on a tablet, comprising:

a source for irradiating a tablet with radiation having at least one frequency in the range from 40 GHz to 100 THz;

a detector for detecting radiation which has been transmitted through or reflected by the tablet;

means for determining a parameter from the detected radiation indicative of the density of a coating layer of the tablet; and means for determining information about the dissolution characteristics of the tablet from said parameter.

The source is a preferably a source of pulsed radiation.

The means for determining a parameter indicative of the density of a coating layer of the tablet may comprise means for determining the time of flight of radiation through said coating layer.

The means for determining a parameter indicative of the density of a coating layer of the tablet may comprise means for determining the strength of the reflected radiation signal.

The apparatus may comprise a robotic arm to allow movement of the tablet.

In a fifth aspect, the present invention provides a method of performing or predicting dissolution analysis on a tablet, the method comprising:

irradiating a tablet with pulsed radiation having at least one frequency in the range from 40 GHz to 100 THz;

detecting radiation which has been transmitted through or reflected by the tablet;

identifying detected radiation in terms of penetration depth of radiation within said tablet;

plotting a quantity at least related to the amplitude of the detected radiation for a plurality of points in a plane substantially perpendicular to the direction of radiation incident on said tablet to obtain an image; and deriving information about the dissolution of the tablet from said image.

There are a variety of other attributes which can be studied using terahertz and hence use to assess/predict likely dissolution rates. For example, core integrity and density changes, chemical distribution of APIs and excipients. Similarly, lack of water ingression or segregation of APIs/excipients can be used to identify tablets with favourable dissolution properties.

In a sixth aspect, the present invention provides a method of performing or predicting dissolution analysis on a tablet, the method comprising:

irradiating a tablet with pulsed radiation having at least one frequency in the range from 40 GHz to 100 THz;

detecting radiation which has been transmitted through or reflected by the tablet;

identifying detected radiation in terms of penetration depth of radiation within said tablet;

plotting a quantity at least related to the amplitude of the detected radiation for a plurality of points in a plane substantially perpendicular to the direction of radiation incident on said tablet to obtain an image; and deriving information about the dissolution of the tablet from said image.

The quantity, which is at least related to the amplitude of the detected radiation, may be plotted as a slice through the tablet at a single depth or the quantity may be plotted for a plurality of depths to form a volumetric map of said tablet. The data for a plurality of depths may be plotted in 3D or it may be mapped onto a 2D plane. For example, the maximum interface index (measured as a function of penetration depth) for each point may be plotted on a 2D plane.

Preferably, the method is performed by using radiation which has been reflected from the tablet. In terahertz analysis, a preferred way of looking at the signal from a particular depth is to look at the delay time of a pulse which has been reflected from a structure.

It is possible to determine whether or not a tablet has the desired dissolution properties by comparing a terahertz image taken at a particular depth from one tablet with known good dissolution properties with that of a tablet being tested. The terahertz image of the tablet being tested should be taken at the same depth as the terahertz image taken for the tablet with the known good dissolution profile.

Similarly, 3D volumetric maps may be compared between a test tablet and a tablet with a known good dissolution profile.

The amplitude of the detected radiation may be measured. Alternatively, the interface index may be used. The interface index is calculated by measuring the amplitude of the radiation reflected from a predetermined depth of this tablet and dividing it by the amplitude of radiation reflected from an interface which lies closer to the external interface of the tablet through which radiation enters the tablet. Typically, the amplitude of radiation reflected from said predetermined depth is divided by the amplitude of radiation reflected from the external interface of the tablet through which the radiation first enters the tablet.

The interface index is an example of a quantity related to the amplitude of the detected radiation. Other examples include, but are not limited to, the refractive index, absorption index and corrections or normalisation of the original amplitude data. The amplitude itself may also be studied.

The technique may be used to image the coating layers of the tablet.

There are a number of ways for example of using coating parameters to obtain further information about dissolution characteristics. A few examples are given below:

a simple visual evaluation of the images of coating thickness across tablet surfaces could be correlated with the onset time and dissolution profile a histogram of coating thickness that looks at the whole tablet layer thickness or individual surfaces could be used to predict likely dissolution use mean thicknesses of coating across the whole tablet surface or individual walls Alternatively, or additionally, the core of the tablet may be imaged. Dissolution properties may be indicated by irregularities in the image.

In a seventh aspect, the present invention provides an apparatus configured to perform dissolution analysis on a tablet, the apparatus comprising:
- a source configured to irradiate a tablet with pulsed radiation having at least one frequency in the range from 40 GHz to 100 THz;
- a detector for detecting radiation which has been transmitted through or reflected by the tablet;
- means for identifying detected radiation in terms of penetration depth of radiation within said tablet;
- means for plotting a quantity at least related to the amplitude of the detected radiation for a plurality of points in a plane substantially perpendicular to the direction of radiation incident on said tablet to obtain an image; and
- means for deriving information about the dissolution of the tablet from said image.

In addition to predicting dissolution characteristics of a tablet, terahertz images can also be used to demonstrate delamination or capping in tablets. Tablets are generally produced by pressing two or more layers of powders together. Due to the complex chemical and structural matrix used in controlled and sustained release products in the pharmaceutical industry, these tablets have proved difficult to manufacture in volume with individual batches showing large inconsistencies. This is a serious problem, as the drug may not be interacting with the human body in the way it was intended and either too much or too little of the active compound may be absorbed by the human system in a given time frame.

The present invention has been developed to address the above problem and, in an eighth aspect, the present invention provides a method for studying delamination and capping in a tablet, the method comprising:
- irradiating a tablet with pulsed radiation having at least one frequency in the range from 40 GHz to 100 THz;
- detecting radiation which has been transmitted through or reflected by the tablet;
- identifying detected radiation in terms of penetration depth of radiation within said tablet;
- plotting a quantity at least related to the amplitude of the detected radiation for a plurality of points in a plane substantially perpendicular to the direction of radiation incident on said tablet to obtain an image; and
- analysing said image to determine the presence of cracks or dislocations within the tablet.

Preferably, the tablet is imaged by detecting reflected terahertz radiation. The quantity may be plotted for a single depth as previously described with reference to dissolution studies. Alternatively, the quantity may be plotted for a plurality of depths to form a volumetric map of said tablet as previously described.

Again, the interface index may be plotted to obtain useful images. Preferably, where a tablet has been created by compressing two powders together, delamination and capping are studied by imaging the buried interface between these two powders.

It is believed that delamination will occur if there is a significant variation in the interface index across the buried interface. Generally, a variation of more than 20% in the interface index will indicate a tablet that is subject to delamination.

The method of the eighth aspect of the present invention may also be applied to a method of manufacturing a tablet with a testing procedure. Therefore, in a ninth aspect, the present invention provides a method of manufacturing a tablet, the method comprising:
- pressing at least two powders together to form a tablet with a buried interface;
- irradiating a tablet with pulsed radiation having at least one frequency in the range from 40 GHz to 100 THz;
- detecting radiation which has been transmitted through or reflected by the tablet;
- identifying detected radiation from said buried interface;
- plotting a quantity at least related to the amplitude of the detected radiation for a plurality of points in a plane substantially perpendicular to the direction of radiation incident on said tablet to obtain an image; and
- analysing said image to determine if variations in the amplitude of the detected radiation indicate if the buried interface is cracked or subject to delamination or large changes in density or chemical constituents; and
- rejecting said tablet is said buried interface is cracked or subject to delamination.

The above method may be extended to varying tablet press parameters (the force applied, rate of force applied, duration of force applied, formulation used) and understanding which recipe or set of parameters provides tablets of acceptable quality by examining the Terahertz images.

In a tenth aspect, the present invention provides an apparatus configured to study delamination and capping in a tablet, the apparatus comprising:
- a source for irradiating a tablet with pulsed radiation having at least one frequency in the range from 40 GHz to 100 THz;
- a detector for detecting radiation which has been transmitted through or reflected by the tablet;
- means for identifying detected radiation in terms of penetration depth of radiation within said tablet;
- means for plotting a quantity at least related to the amplitude of the detected radiation for a plurality of points in a plane substantially perpendicular to the direction of radiation incident on said tablet to obtain an image; and
- means for analysing said image to determine the presence of cracks or dislocations within the tablet.

In a eleventh aspect, the present invention provides an apparatus for manufacturing a tablet, the apparatus comprising:
- a press for pressing at least two powders together to form a tablet with a buried interface;
- a source for irradiating a tablet with pulsed radiation having at least one frequency in the range from 40 GHz to 100 THz;
- a detector for detecting radiation which has been transmitted through or reflected by the tablet;
- means for identifying detected radiation from said buried interface;
- means for plotting a quantity at least related to the amplitude of the detected radiation for a plurality of points in a plane substantially perpendicular to the direction of radiation incident on said tablet to obtain an image; and
- means for analysing said image to determine if variations in the amplitude of the detected radiation indicate if the buried interface is cracked or subject to delamination; and rejecting said tablet is said buried interface is cracked or subject to delamination.

The parameters used for pressing said powders together may be varied to reduce the number of tablets which are rejected due to cracks, delaminations or dislocations.

Terahertz radiation may also be used to investigate water ingression in two tablets.

Water contamination is also a serious issue which affects the pharmaceutical industry. The presence of water leads to issues with tablet dissolution during design, manufacturing and testing, as well as tablet stability after manufacture and during storage; these issues can affect product efficacy and safety. The migration of water from tablet cores into the coatings, or coatings to the surface is also an important issue. It is difficult to determine water ingression into a tablet without performing a destructive test.

Therefore, in a twelfth aspect, the present invention provides a method of determining water ingression into a tablet, the method comprising:
  irradiating a tablet with pulsed radiation having at least one frequency in the range from 40 GHz to 100 THz;
  detecting radiation which has been transmitted through or reflected by the tablet;
  identifying detected radiation in terms of penetration depth of radiation within said tablet;
  plotting a quantity at least related to the amplitude of the detected radiation for a plurality of points to obtain an image; and
  deriving information about water ingression by identifying areas of high absorption within said tablet.

Preferably, the image is produced by plotting the quantity at a plurality of points substantially parallel to the direction of incident radiation. In other words, the image is generated by using a time domain trace which has been scanned in one dimension.

The image may also be constructed using the refractive index. This may be used by producing an image in a plane substantially perpendicular to the direction of incident radiation. Such an image may be generated by plotting data for a single delay time on the time domain trace.

Spectral information may also be determined in order to verify that the contaminant is water.

Analysis in the time domain can also be used to study or detect water ingression. The shape of the reflected waveform from a region containing water is characterised by a broad profile in the time domain. Alternatively, a decrease in peak height of the Terahertz pulse in a region known to be contaminated with water can be used to determine the amount of water.

In a thirteenth aspect, the present invention provides an apparatus for determining water ingression into a tablet, the apparatus comprising:
  a source for irradiating a tablet with pulsed radiation having at least one frequency in the range from 40 GHz to 100 THz;
  a detector for detecting radiation which has been transmitted through or reflected by the tablet;
  means for identifying detected radiation in terms of penetration depth of radiation within said tablet;
  means for plotting a quantity at least related to the amplitude of the detected radiation for a plurality of points to obtain an image; and
  means for deriving information about water ingression by identifying areas of high absorption within said tablet.

Another problem which occurs when manufacturing tablets is that the active pharmaceutical ingredient (API) and/or excipients in the coatings or core may become segregated and aggregate into clumps. This aggregation is again generally not possible to determine without destructive tests of the sample.

Therefore, the present invention has been developed to address this problem and, in an fourteenth aspect, provides a method of determining the distribution of an active pharmaceutical ingredient (API) and/or excipient distribution within a tablet, the method comprising:
  irradiating a tablet with pulsed radiation having at least one frequency in the range from 40 GHz to 100 THz;
  detecting radiation which has been transmitted through or reflected by the tablet; identifying detected radiation in terms of penetration depth of radiation within said tablet;
  plotting a quantity at least related to the amplitude of the detected radiation for a plurality of points to obtain an image;
  reviewing the image to establish if the API and/or excipient has formed into clumps or segregated into regions.

The images may be preferably constructed using reflected radiation. They may be produced using points substantially parallel to the direction of incident radiation. This may be achieved as previously described by scanning a time domain trace in one dimension across the sample.

The image may also be generated points by taking points in a plane substantially perpendicular to the direction of incident radiation. This may be achieved by looking at the terahertz waveform for a particular delay time.

Spectral information may also be used in order to study particular clumps to determine if they are excipients or API or a combination of the two. This may be achieved by obtaining a terahertz spectra from the region of a clump and comparing it with a known spectra. Both absorption and/or refractive index information can be used.

In a fifteenth aspect, the present invention provides an apparatus for the distribution of an active pharmaceutical ingredient (API) and/or excipient distribution within a tablet, the apparatus comprising:
  a source for irradiating a tablet with pulsed radiation having at least one frequency in the range from 40 GHz to 100 THz;
  a detector for detecting radiation which has been transmitted through or reflected by the tablet;
  means for identifying detected radiation in terms of penetration depth of radiation within said tablet;
  means for plotting a quantity at least related to the amplitude of the detected radiation for a plurality of points to obtain an image;
  means for reviewing the image to establish if the API and/or excipient has formed into clumps or segregated into regions.

Today, almost all pharmaceutical tablets are produced by compressing powder mixtures together. The quality of the final product heavily relies on a physical morphology (particle size uniformity of the particles in the mixture). Therefore, it is desirable to monitor and control the particle properties.

The particle sizes of most pharmaceutical materials are in the range of a few micrometers to tens of micrometers. This prohibits the use of visible light technology to assess particle sizes as light scattering is too strong.

The present invention has been developed to address this problem and, according to an sixteenth aspect provides a method of determining the size of particles within a tablet, the method comprising:
  irradiating a tablet with pulsed radiation having at least one frequency in the range from 40 GHz to 100 THz;
  detecting radiation which has been transmitted through or reflected by the tablet to establish $E_{samp}^{THz}(t)$, which is the amplitude of the electric field of the measured THz radiation over time (t);

irradiating a reference sample with pulsed radiation having at least one frequency in the range from 40 GHz to 100 THz;

detecting radiation which has been transmitted through or reflected by the reference to establish $E_{ref}^{THz}(t)$, which is the amplitude of the electric field of the measured THz radiation over time (t);

calculating the extinction spectra:

$$\varepsilon(\nu) = -2\log_{10}\left(\int_{-\infty}^{\infty} E_{samp}^{THz}(t)e^{j2\pi\nu t}dt \bigg/ \int_{-\infty}^{\infty} E_{ref}^{THz}(t)e^{j2\pi\nu t}dt\right)$$

where ν is the frequency; and plotting said extinction spectra to determine information about the particle sizes within said tablet.

The terahertz radiation can perform this function because it utilises much longer wavelengths and is therefore less prone to scattering by micro-size particles. Further, terahertz radiation can penetrate into the region of interest even in strongly scattering mediums.

In a particularly preferred embodiment, particle sizes may be derived by fitting the extinction spectra derived above to the equation $$\epsilon(\nu) = B\nu^A$$

where B and A are constants to be fitted and B is an indication of the particle size.

In a seventeenth aspect, the present invention provides an apparatus for determining the size of particles within a tablet, the apparatus comprising:

a source irradiating a tablet and a reference sample with pulsed radiation having at least one frequency in the range from 40 GHz to 100 THz;

a detector for detecting radiation which has been transmitted through or reflected by the tablet to establish $E_{samp}^{THz}(t)$, which is the amplitude of the electric field of the measured THz radiation over time (t) and for detecting radiation which has been transmitted through or reflected by the reference to establish $E_{ref}^{THz}(t)$, which is the amplitude of the electric field of the measured THz radiation over time (t);

means for calculating the extinction spectra:

$$\varepsilon(\nu) = -2\log_{10}\left(\int_{-\infty}^{\infty} E_{samp}^{THz}(t)e^{j2\pi\nu t}dt \bigg/ \int_{-\infty}^{\infty} E_{ref}^{THz}(t)e^{j2\pi\nu t}dt\right)$$

where ν is the frequency; and means for plotting said extinction spectra to determine information about the particle sizes within said tablet.

It is desirable when analysing chemical samples to be able to demonstrate how the different chemical components are distributed within a tablet. Therefore, in a eighteenth aspect, the present invention provides a method of determining the spatial distribution of a component in a tablet, the method comprising:

irradiating a tablet at a plurality of spatial points across the tablet with pulsed radiation having at least one frequency in the range from 40 GHz to 100 THz;

detecting radiation which has been transmitted through or reflected by the tablet;

representing the radiation detected for each spatial point as a pixel vector p, where:

$\vec{p} = [p_1, p_2, \ldots, p_n]$ and $p_i$ is the absorption coefficient or refractive index measured at wavelength $\lambda_i$ for the specific pixel and i is an integer from 1 to n where n is an integer of greater than 1;

representing a target vector as $\vec{t} = [t_1, t_2, \ldots, t_n]$ where $t_i$ is the absorption coefficient or refractive index measured at wavelength $\lambda_i$ for said component; and comparing the pixel vector with the target vector at each spatial point and plotting a measure of this comparison.

The pixel vector may be compared with a target vector by calculating $Ed_{orig}$:

$$Ed_{orig} = \sqrt{\sum_{i=1}^{n}(t_i - p_i)^2}$$

A further method of comparing the pixel vector with the target vector is to calculate ρ:

$$\rho = \frac{1}{1-n}\left(\frac{\sum_{i=1}^{n}(t_i - \mu_{ti})(p_i - \mu_{pi})}{\sigma_t \sigma_p}\right)$$

where $\mu_p$ and $\sigma_p$ are the mean and standard deviation of the pixel vector respectively and $\mu_t$ and $\sigma_t$ are the mean and standard deviation of the target vector respectively.

A further method is to combine the above two methods and calculate SSV:

$$SSV = \sqrt{Ed^2 + (1-\rho)^2}$$

where:

$Ed = (Ed_{orig} - m)/(M-m)$ and m and M are the minima and maximum of $Ed_{orig}$ values respectively.

Finally, a further method to compare the pixel vector with the target vector is to calculate α:

$$\alpha = \arccos\left(\frac{\sum_{i=1}^{n} t_i p_i}{\sqrt{\sum_{i=1}^{n} t_i^2} \sqrt{\sum_{i=1}^{n} p_i^2}}\right)$$

In a ninteenth aspect, the present invention provides an apparatus for determining the spatial distribution of a component in a tablet, the method comprising:

a source for irradiating a tablet at a plurality of spatial points across the tablet with pulsed radiation having at least one frequency in the range from 40 GHz to 100 THz;

a detector for detecting radiation which has been transmitted through or reflected by the tablet;

means for representing the radiation detected for each spatial point as a pixel vector p, where:

$\vec{p} = [p_1, p_2, \ldots, p_n]$ and $p_i$ is the absorption coefficient or refractive index measured at wavelength $\lambda_i$ for the specific pixel and i is an integer from 1 to n where n is an integer of greater than 1;

representing a target vector as $\vec{t}[t_1, t_2, \ldots, t_n]$ where $t_i$ is the absorption coefficient or refractive index measured at wavelength $\lambda_i$ for said component; and comparing the pixel vector with the target vector at each spatial point and plotting a measure of this comparison.

The techniques described above may be combined with any of the techniques described in the applicant's earlier patent applications and specifically GB 2 397 207, GB 2 405 466 and GB 2 405 200. For example, many of the above aspects of the invention may be practised using a detector positioned so as to reduce detection of specular radiation as described in GB2 405 200, or to maintain a predetermined distance between the emitter and the sample while scanning as described in GB 2 405 466 or using the frequency analysis techniques of GB 2 397 207.

More preferably radiation in the frequency range from 50 GHz to 10 THz is used, even more preferably in the frequency range from 100 GHz to 5 THz.

The present invention will now be described with reference to the following non-limiting embodiments in which.

Figure 5:
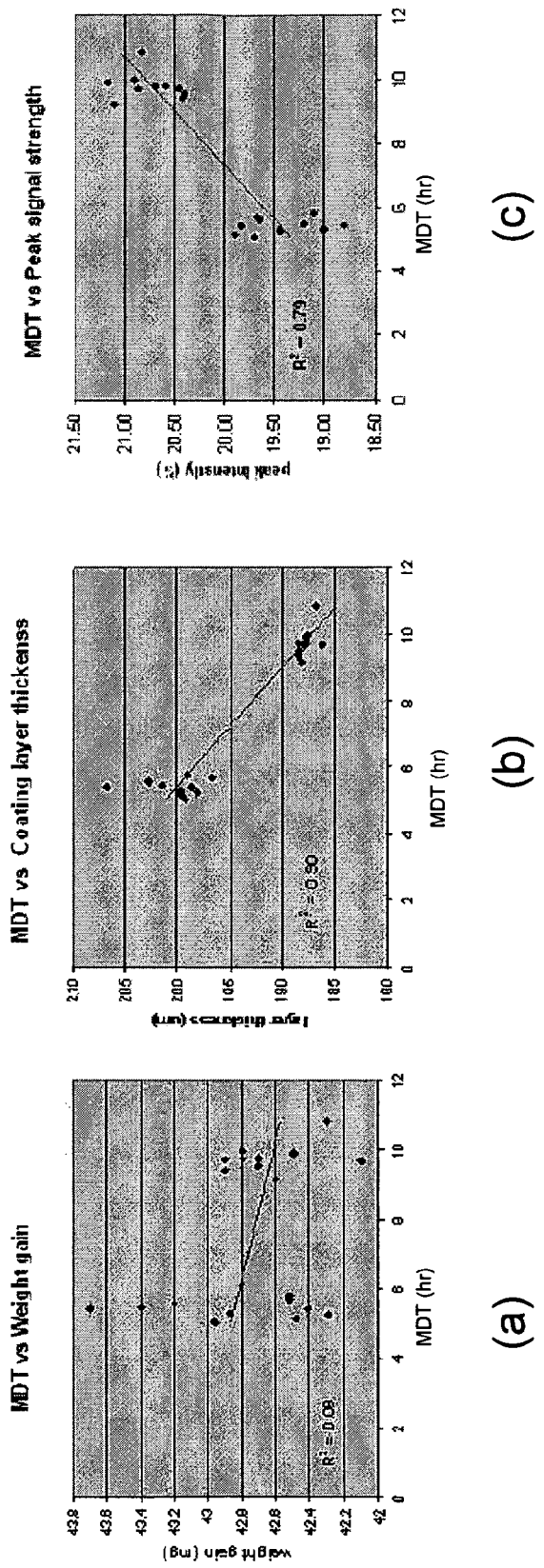
Figure 6:
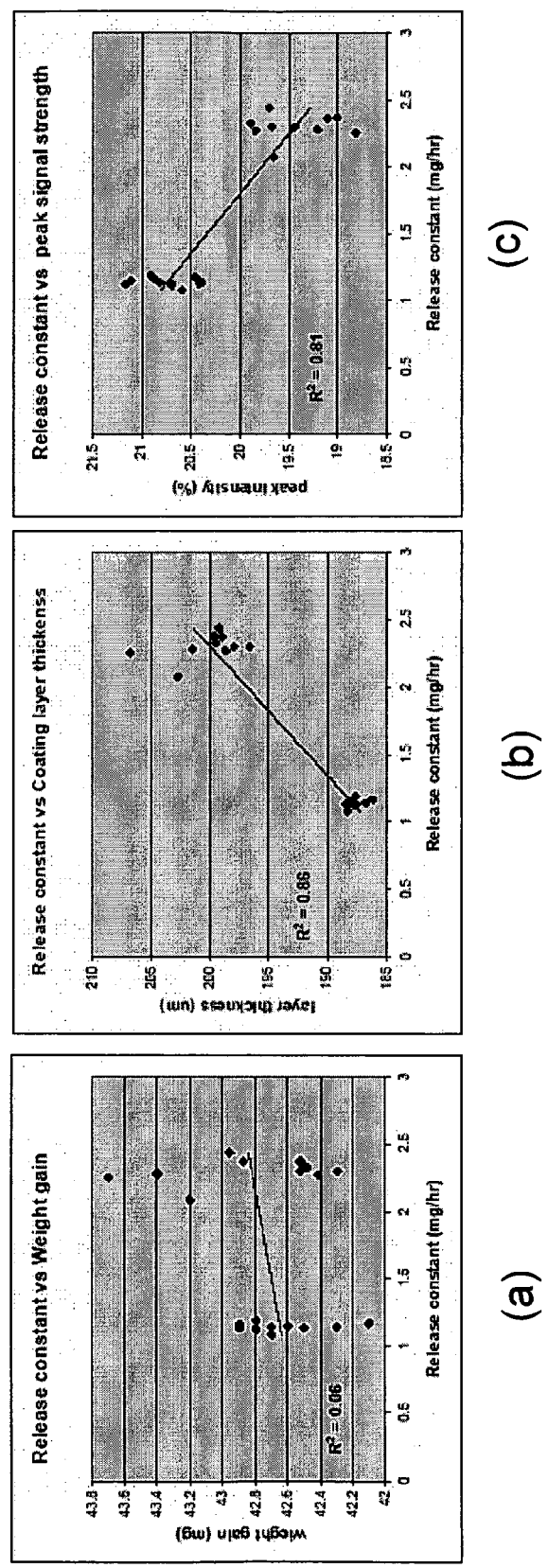
Figure 7:
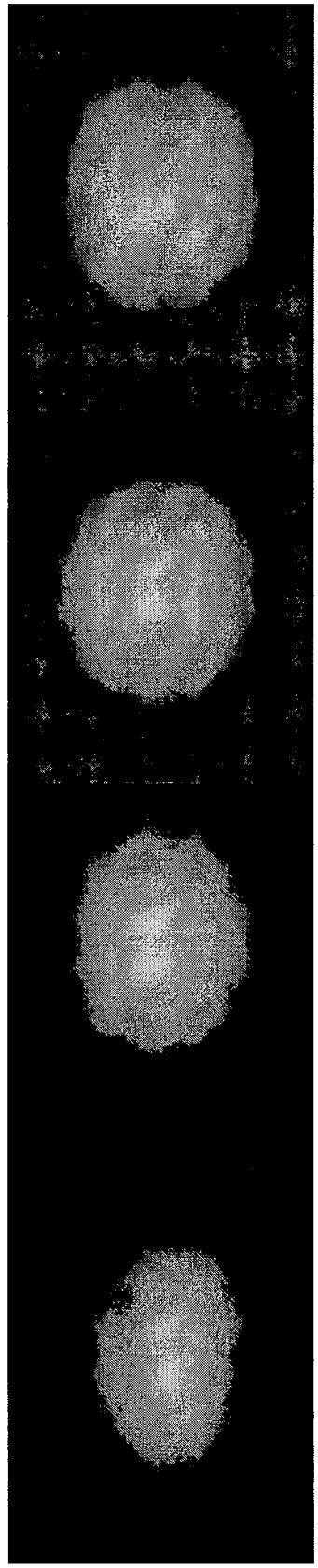
Figure 8:
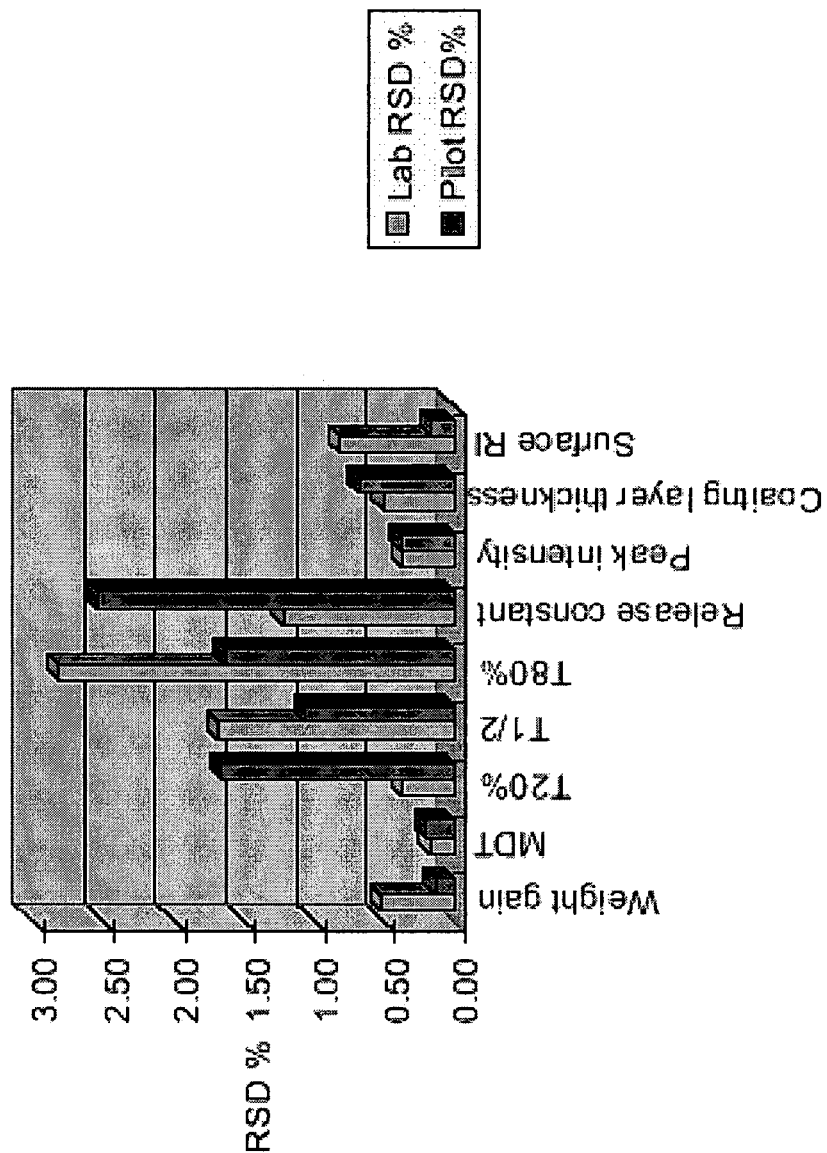
Figure 9:
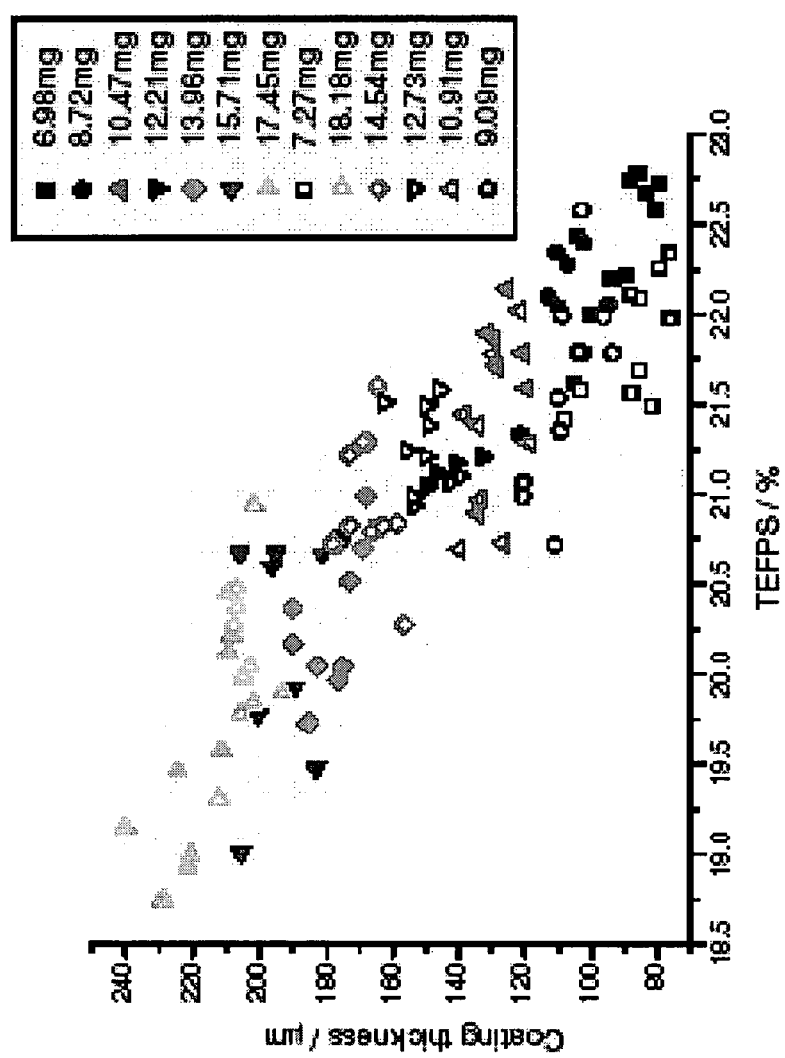
Figure 10:
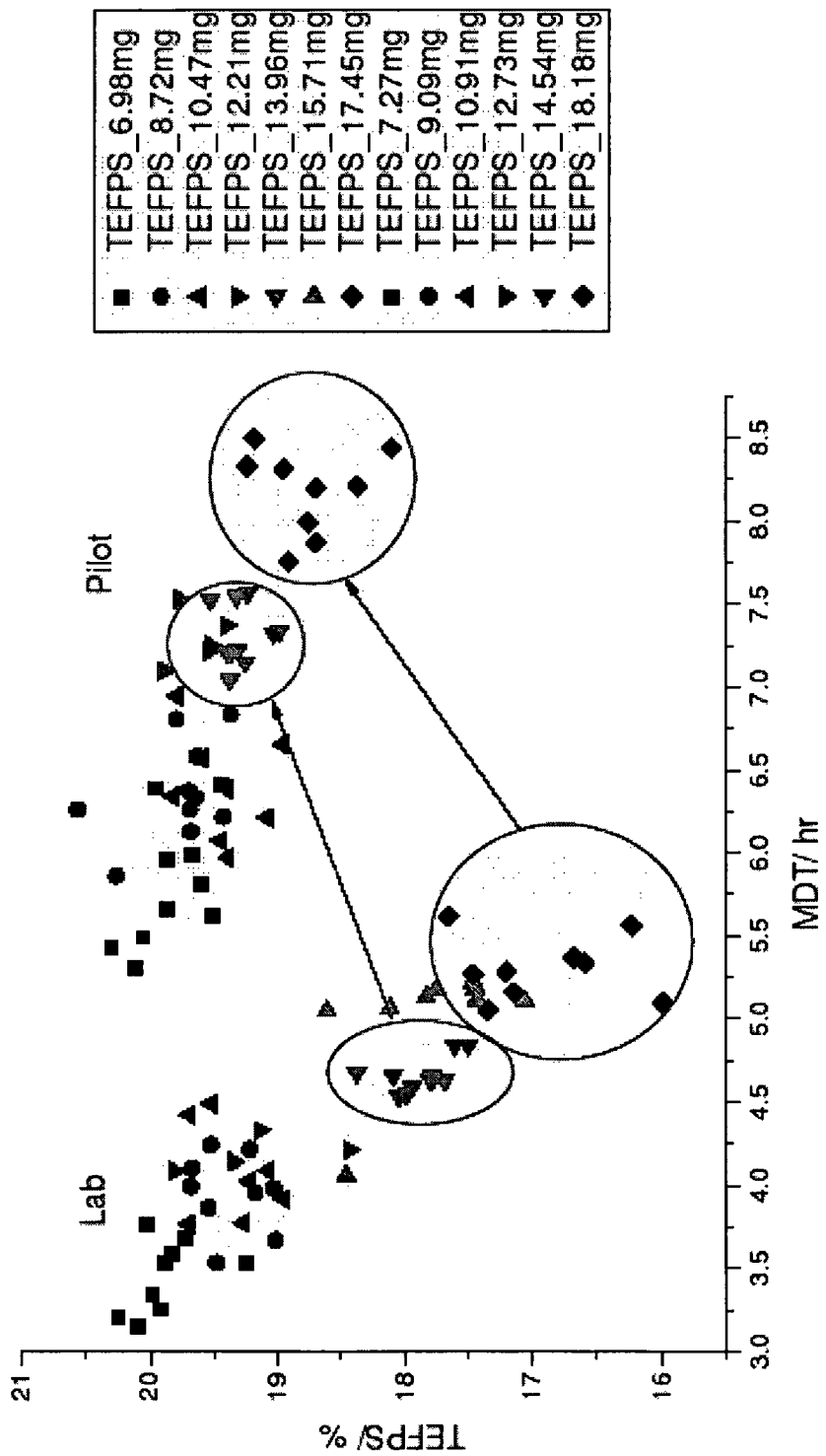
Figure 11:
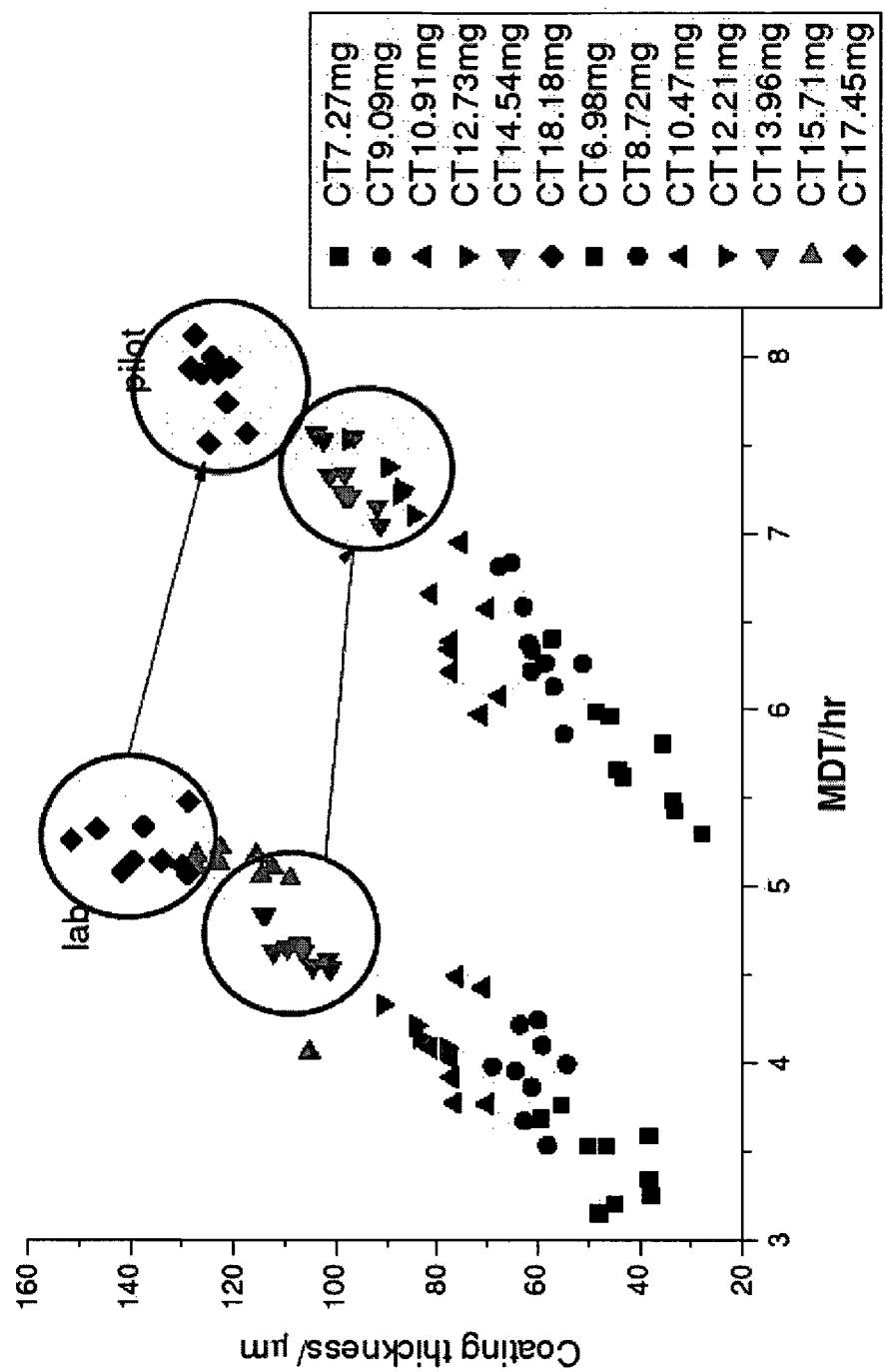
Figure 12:
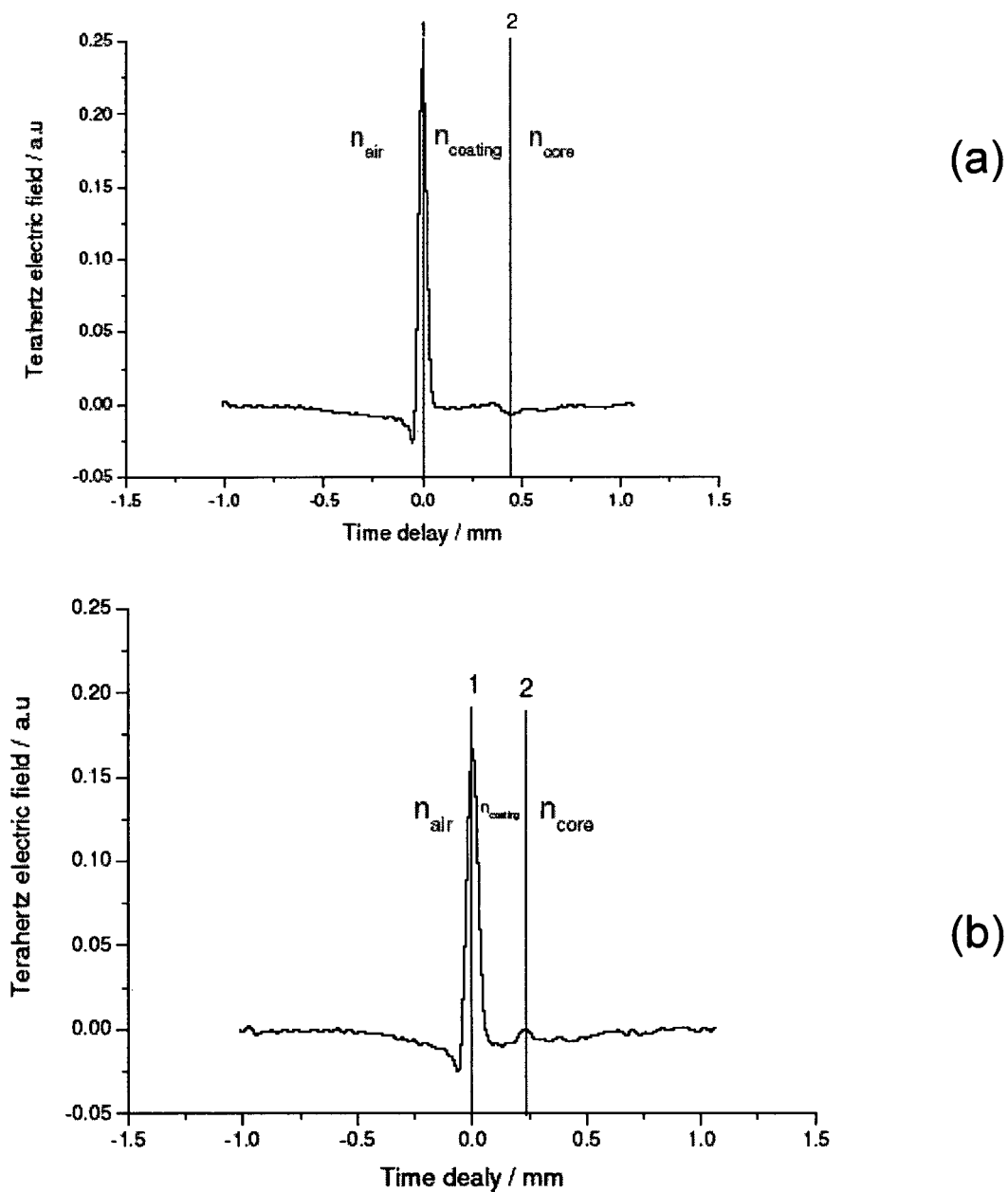
Figure 13:
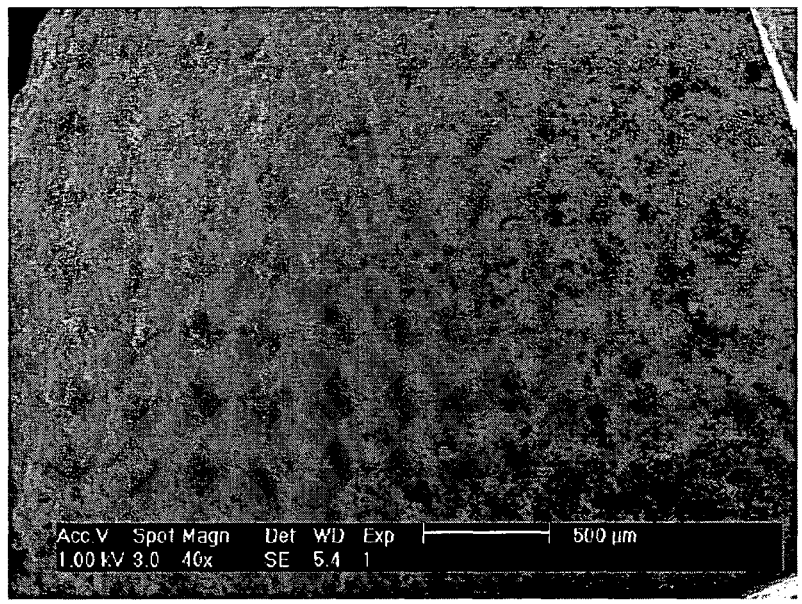
Figure 13:
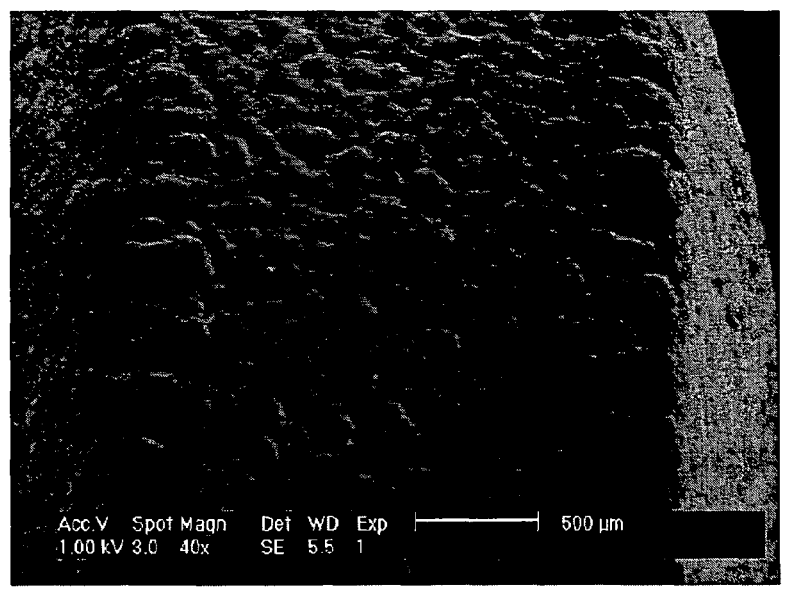
Figure 14:
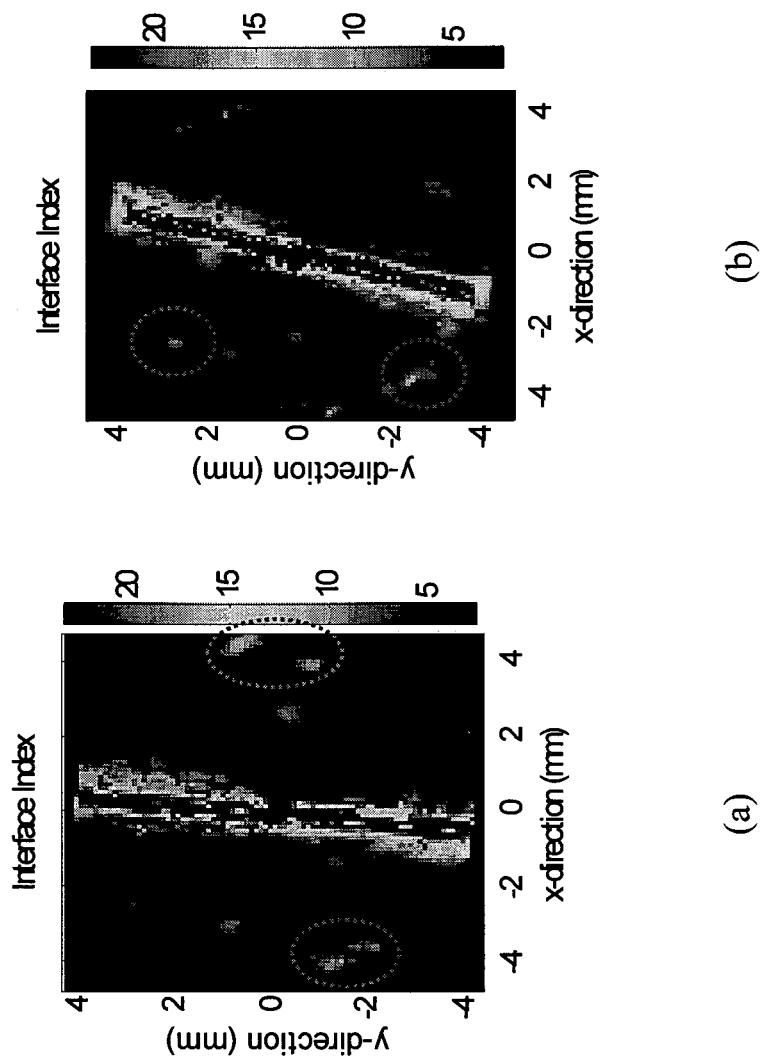
Figure 15:
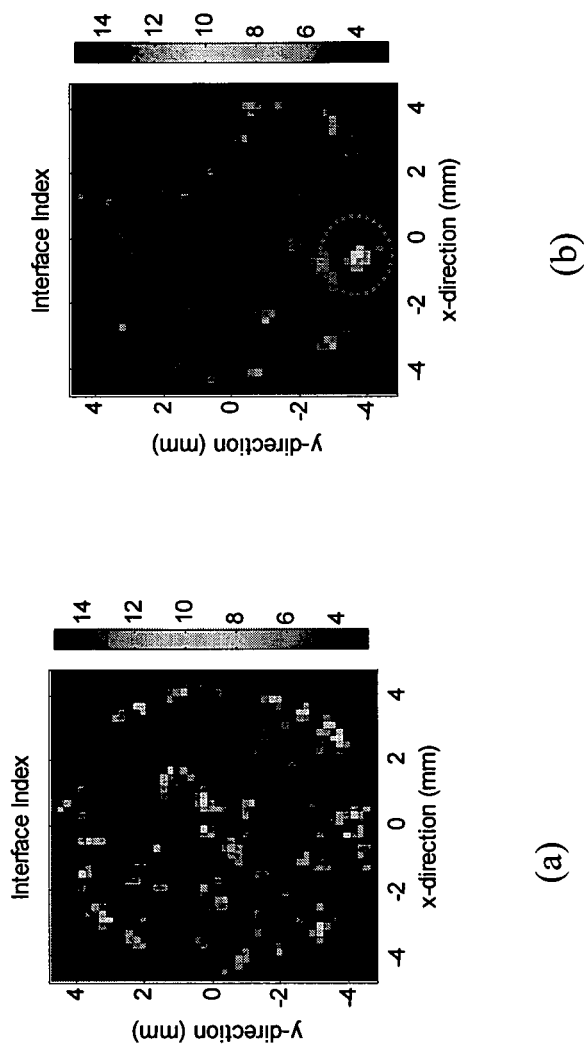
Figure 16:
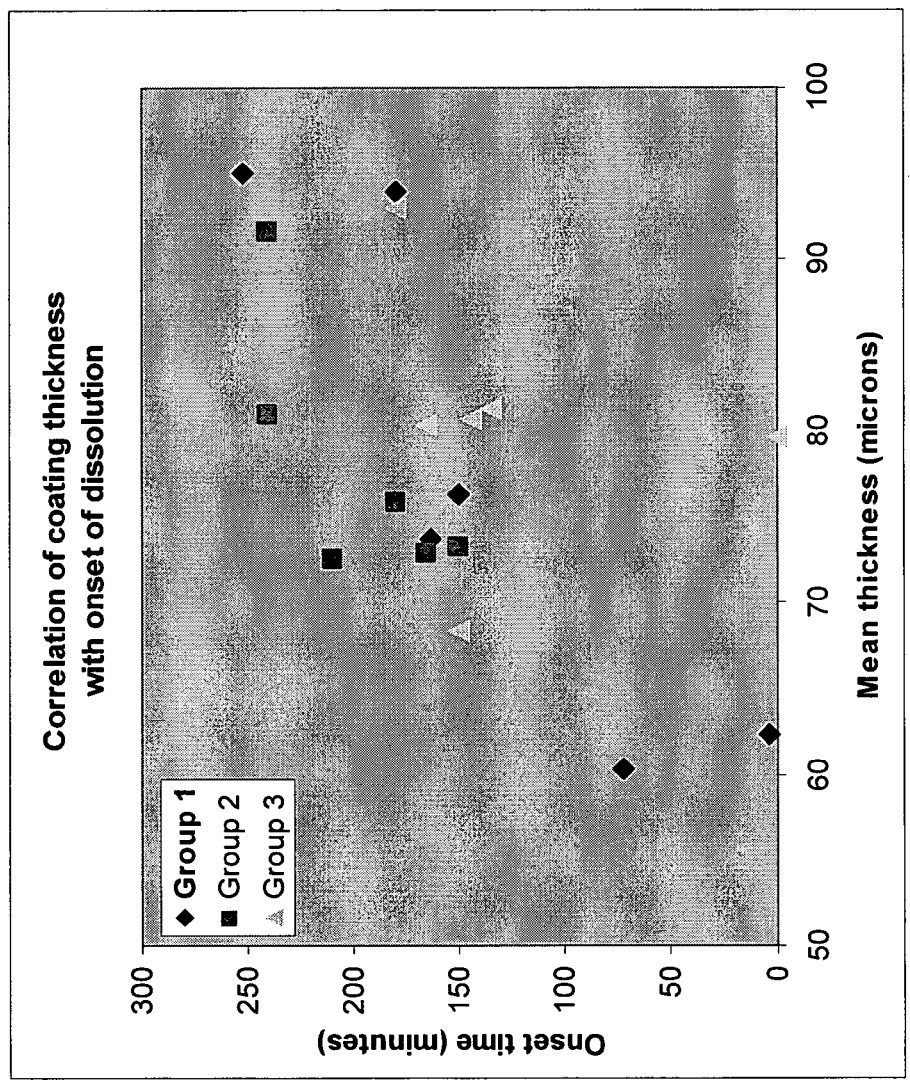
Figure 18:
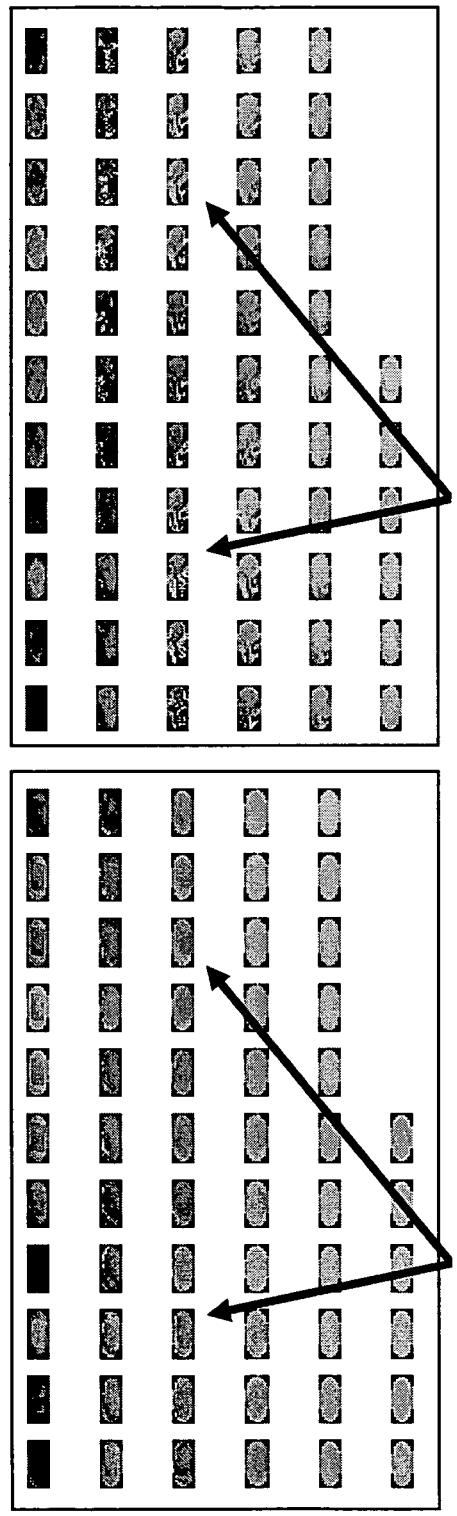
Figure 19:
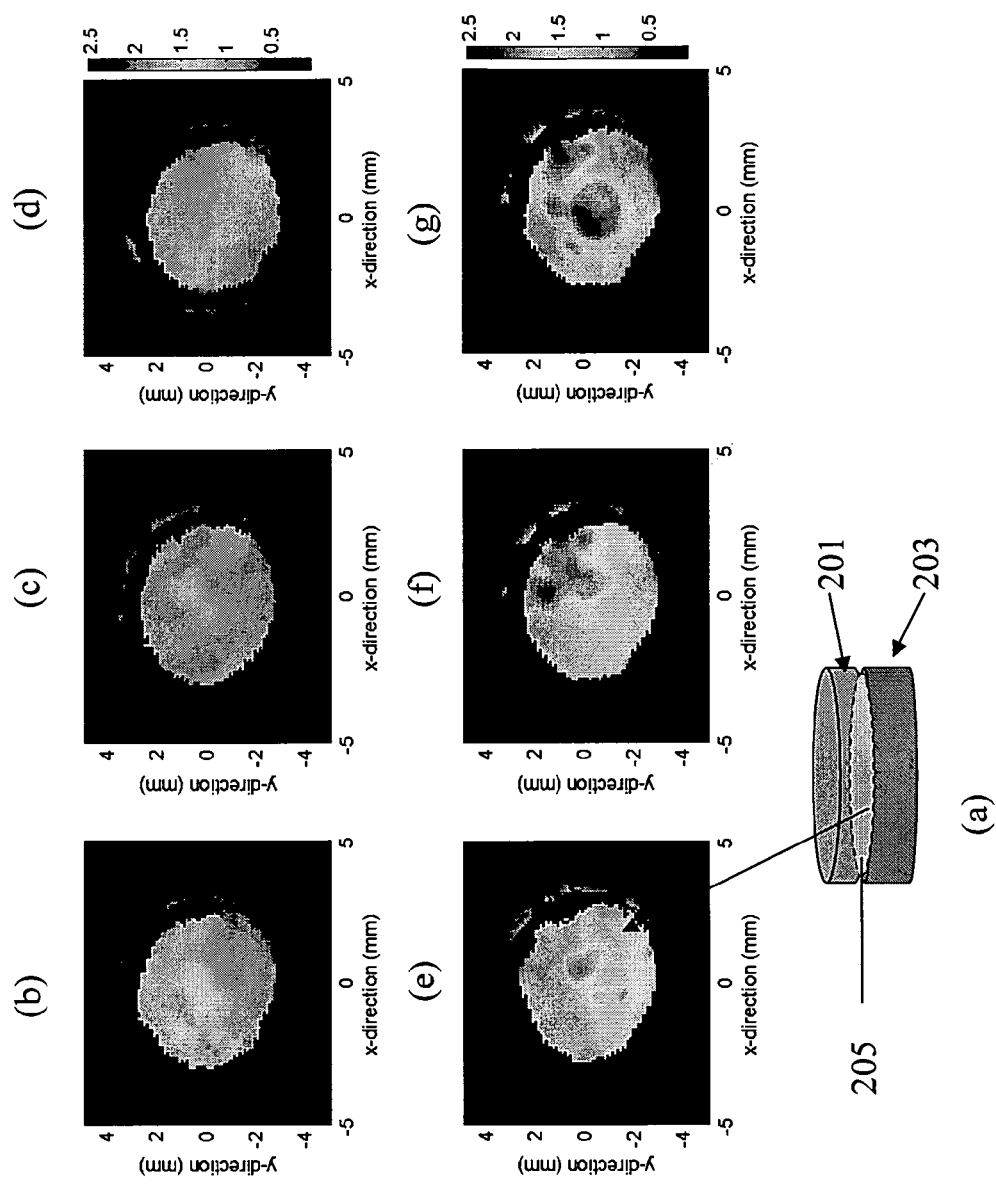
Figure 20:
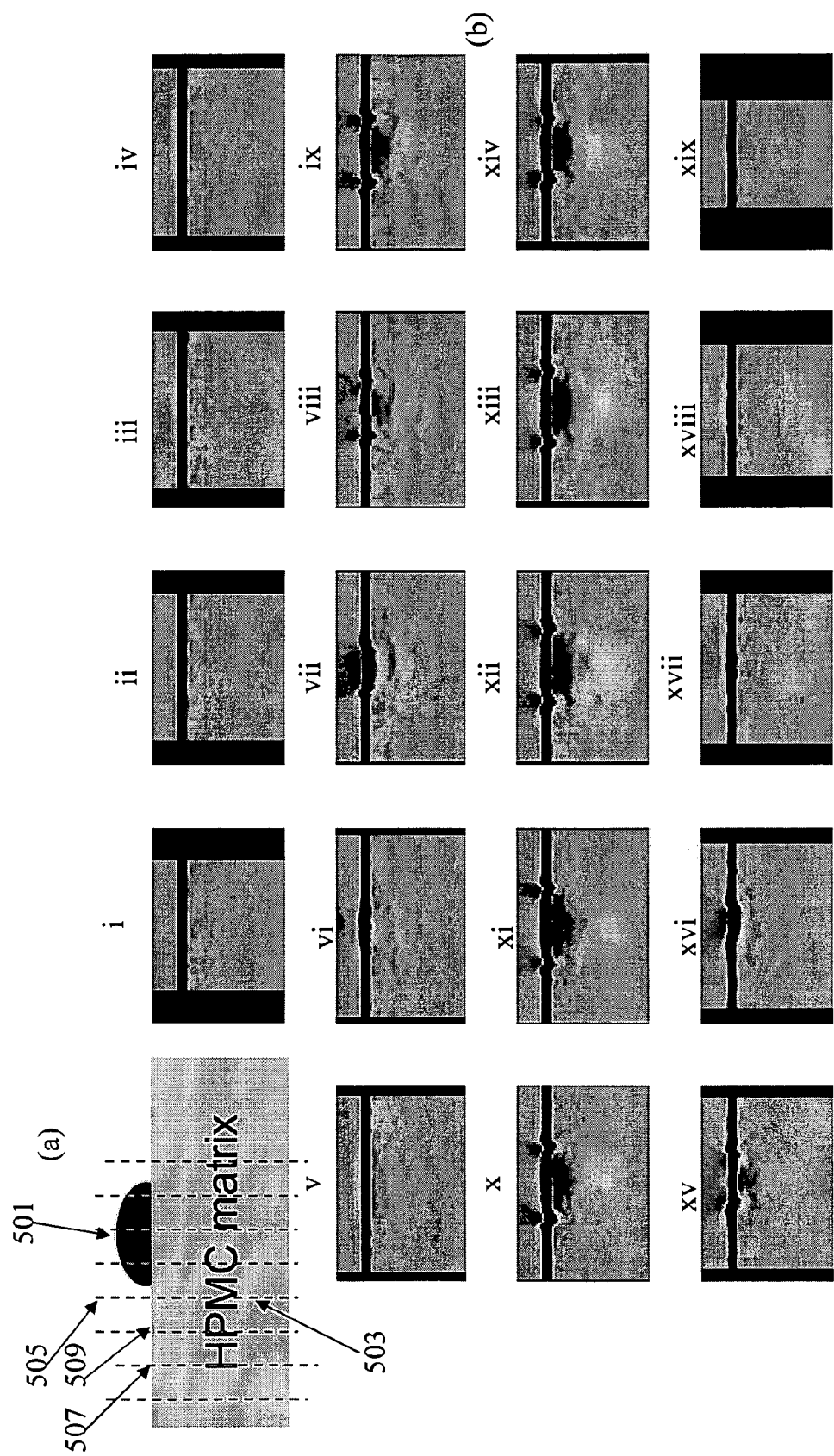
Figure 21:
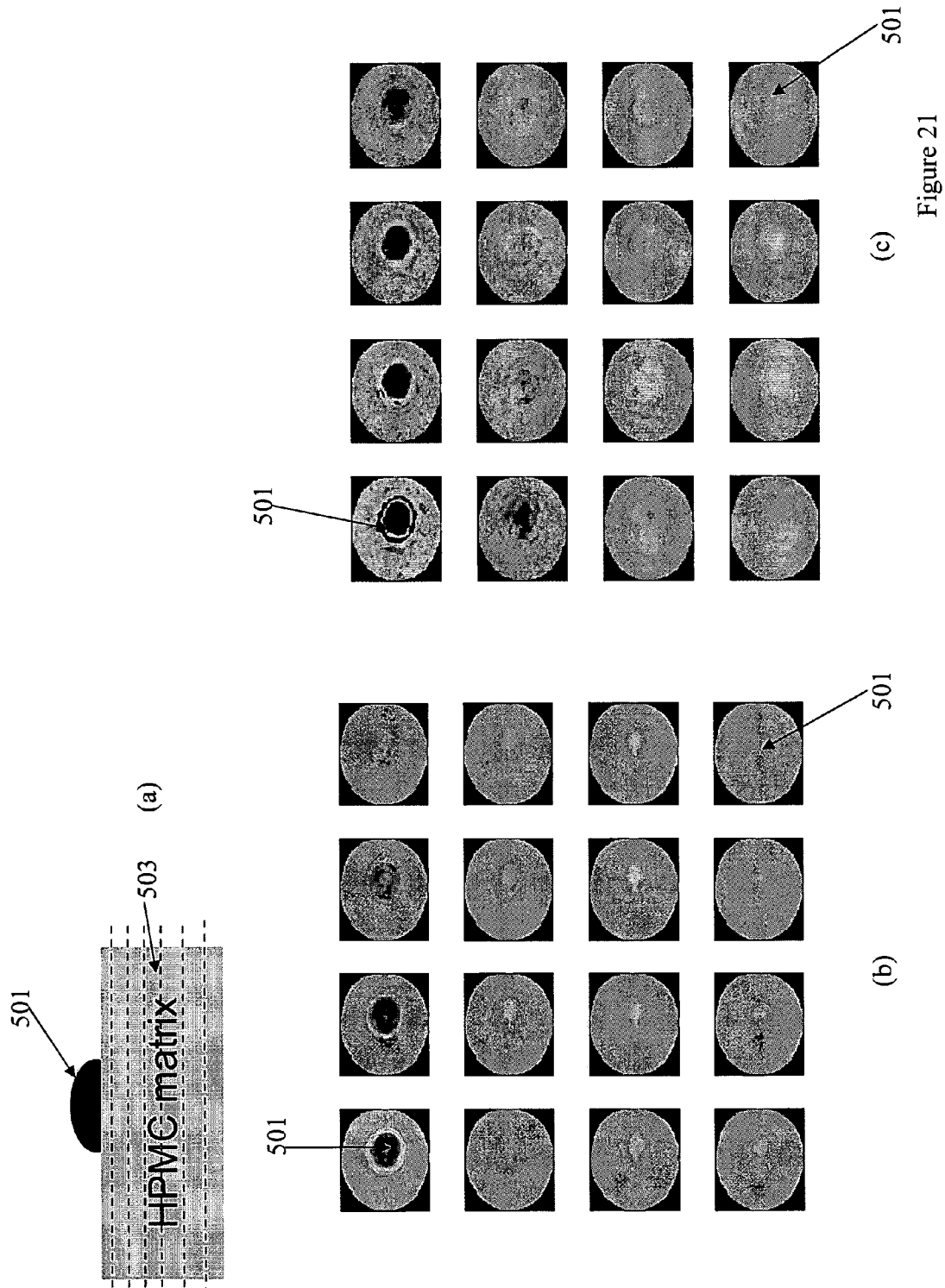
Figure 24:
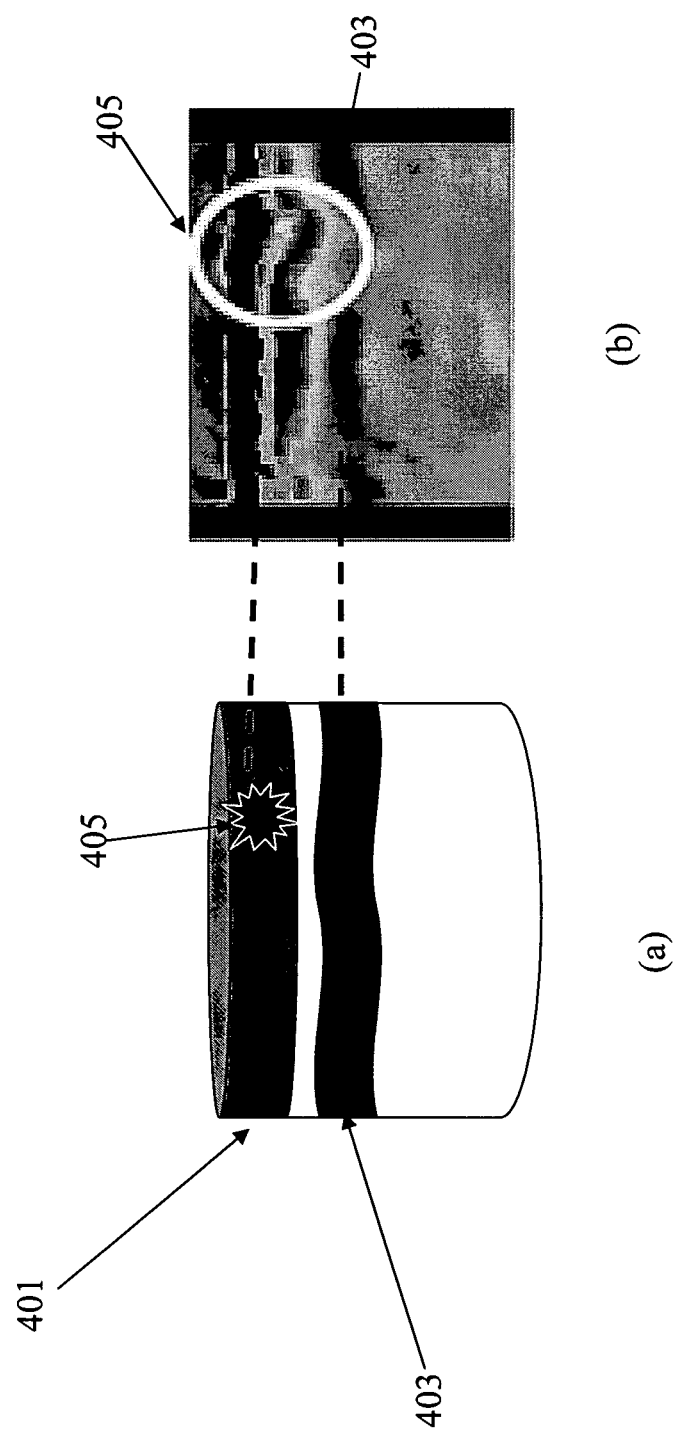
Figure 26:
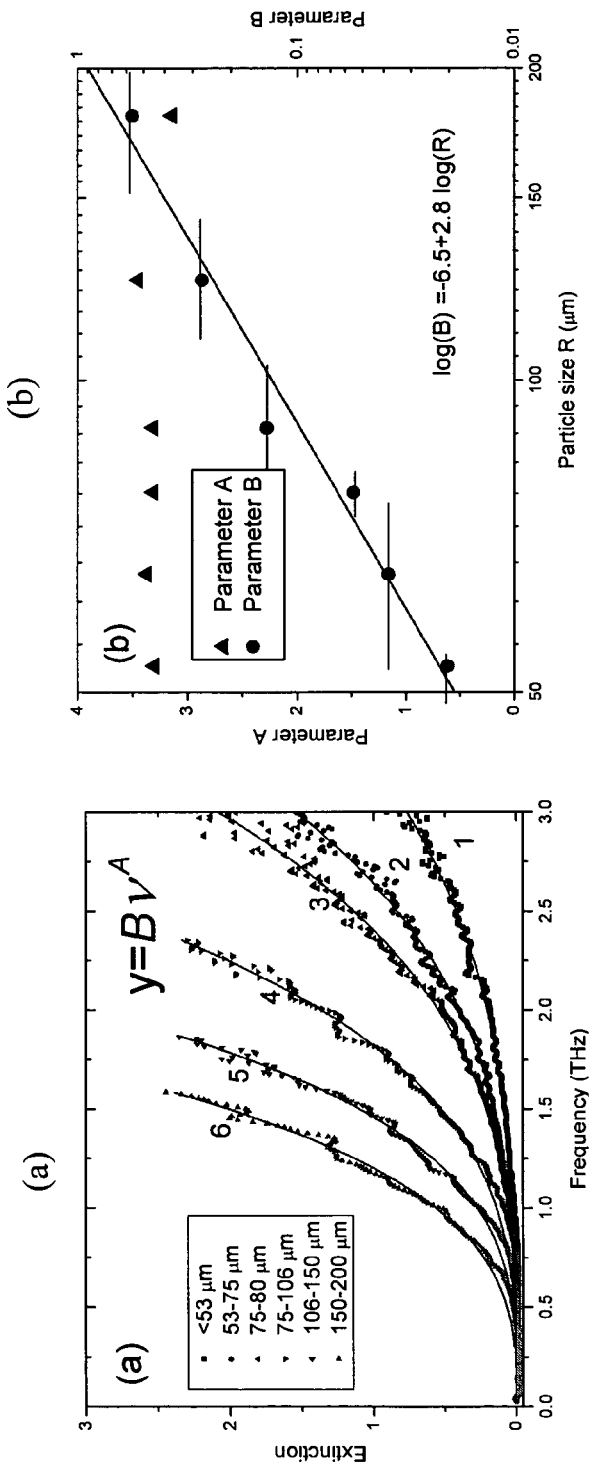

FIG. 5a is a plot showing the correlation between the mean dissolution time of a range of tablets measured using conventional dissolution tests and the weight gain of tablets during the coating process; FIG. 5b is a plot showing the correlation between the mean dissolution time of a range of tablets measured using conventional dissolution tests and the thickness of the coating layer; and FIG. 5c is a plot showing the correlation between the mean dissolution time of a range of tablets measured using conventional dissolution tests and the maximum strength of the reflected THz signal;

FIG. 6a is a plot showing the correlation between the dissolution release constant of a range of tablets measured using conventional dissolution tests and the weight gain of tablets during the coating process; FIG. 6b is a plot showing the correlation between the dissolution release constant of a range of tablets measured using conventional dissolution tests and the thickness of the coating layer; and FIG. 6c is a plot showing the correlation between the dissolution release constant of a range of tablets measured using conventional dissolution tests and the maximum strength of the reflected THz signal;

FIG. 7a is a picture of a sustained release tablet which has been coated with polyvinyl acetate, the picture was taken 2.5 hours into dissolution, FIG. 7b shows the tablet of FIG. 7a after 4.5 hours; FIG. 7c shows the tablet of FIG. 7a after 5.5 hours; and FIG. 7d shows the tablet of FIG. 7a after 7 hours;

FIG. 8 is a plot of the relative standard deviation of various parameters which can be used to indicate dissolutions for tablets prepared on a laboratory scale and tablets prepared on a pilot scale;

FIG. 9 is a plot of the coating thickness against the strength of the reflected THz signal (TEFPS) expressed as a percentage of the signal from a perfect mirror for a range of tablet coating weights;

FIG. 10 is a plot of TEFPS against mean dissolution time (MDT) for the tablets of FIG. 9;

FIG. 11 is a plot of coating thickness against MDT for the tablets of FIGS. 9 and 10;

FIG. 12a is a time domain THz trace for a tablet measured on the top or bottom surfaces and FIG. 12b is a time domain trace for the same tablet as FIG. 12a, but measured on the central band;

FIG. 13a is a SEM image of the top or bottom surface of a sustained release tablet and FIG. 13b is a SEM image of the same tablet as 13a, but taken at the central band;

FIG. 14a is a terahertz image of a tablet showing good dissolution profile and FIG. 14b is a terahertz image of a tablet with poorer dissolution characteristics;

FIG. 15a is a terahertz image of a tablet which has good dissolution properties and FIG. 15b is a terahertz image of a tablet having poorer dissolution properties;

FIG. 16 is a plot of the onset time to dissolution against mean thickness of a tablet coating;

FIG. 17a is a schematic of a tablet with no cracks, FIGS. 17b and 17c are terahertz images of the tablet of FIG. 17a, FIG. 17d is a schematic of a tablet with cracks and FIGS. 17e and 17f are terahertz images showing the presence of the cracks in the tablet of FIG. 17d;

FIG. 18a is a series of terahertz images for different depths for a tablet showing the presence of minor defects but generally uniform structure, FIG. 18b is again a series of terahertz images taken through a sample this time showing the presence of cracks;

FIG. 19a is a schematic showing two active pharmaceutical ingredients or excipient layers which have been pushed together to form a buried interface, FIGS. 19b, 19c and 19d show THz images of the buried interface in good quality tablets and FIGS. 19e, 19f and 19g show THz images of a buried interface for poorer quality tablets;

FIG. 20a is a schematic of a hydroxypropyl methyl cellulose (HPMC) matrix with a water droplet, and FIG. 20b is a series of THz images showing vertical cross sections through the matrix of FIG. 20a;

FIG. 21a is a further schematic of a HPMC matrix with a water droplet, FIG. 21b are plots of the refractive index derived from THz measurements for horizontal cross sections through the matrix of FIG. 21a, and FIG. 21c are plots showing changes in the refractive index for horizontal cross sections of the matrix of FIG. 21a;

FIG. 22a is a schematic of a cross-section of a tablet, FIG. 22b is a schematic of a tablet, and FIG. 22c is a plot of the amplitude of a terahertz signal against time for a tablet showing features due to water absorption;

FIGS. 23a and 23b are identical to FIGS. 22a and 22b, and FIG. 23c is an image based on data obtained by performing a linear scan of a point on the tablet of FIG. 22b showing the presence of water;

FIG. 24a is a schematic of a tablet which suffered API segregation and FIG. 24b is a corresponding terahertz image;

FIG. 25a is a visible light picture of a tablet, FIG. 25b is a schematic of clumps of excipient and active pharmaceutical ingredients (API) inside the tablet of FIG. 25a, FIG. 25c is a cross-section terahertz image of the tablet showing no aggregates, FIG. 25d is a cross-section through the tablet of FIG. 25a showing aggregates and FIGS. 25e and 25f are terahertz spectra of known chemicals showing how the aggregates shown in FIG. 25d may be identified;

FIG. 26a is a plot of extinction spectra against frequency for a plurality of tablets with different powder sizes and FIG. 26b is a plot of the parameters used to model the spectra of FIG. 26a against actual particle size; and FIG. 27a is a frequency spectra of the absorption of pure Theophyline, pure Lactose and pure MCC and FIG. 27b is the corresponding frequency spectra of the refractive index of these components, FIGS. 27c, d, e and f are cosine correlation mapping results using absorption of a tablet for the components shown in FIG. 27a and FIGS. 27g, h, i, j are cosine correlation mapping results using refractive index of a tablet for the components shown in FIG. 27b.

Figure 1A:
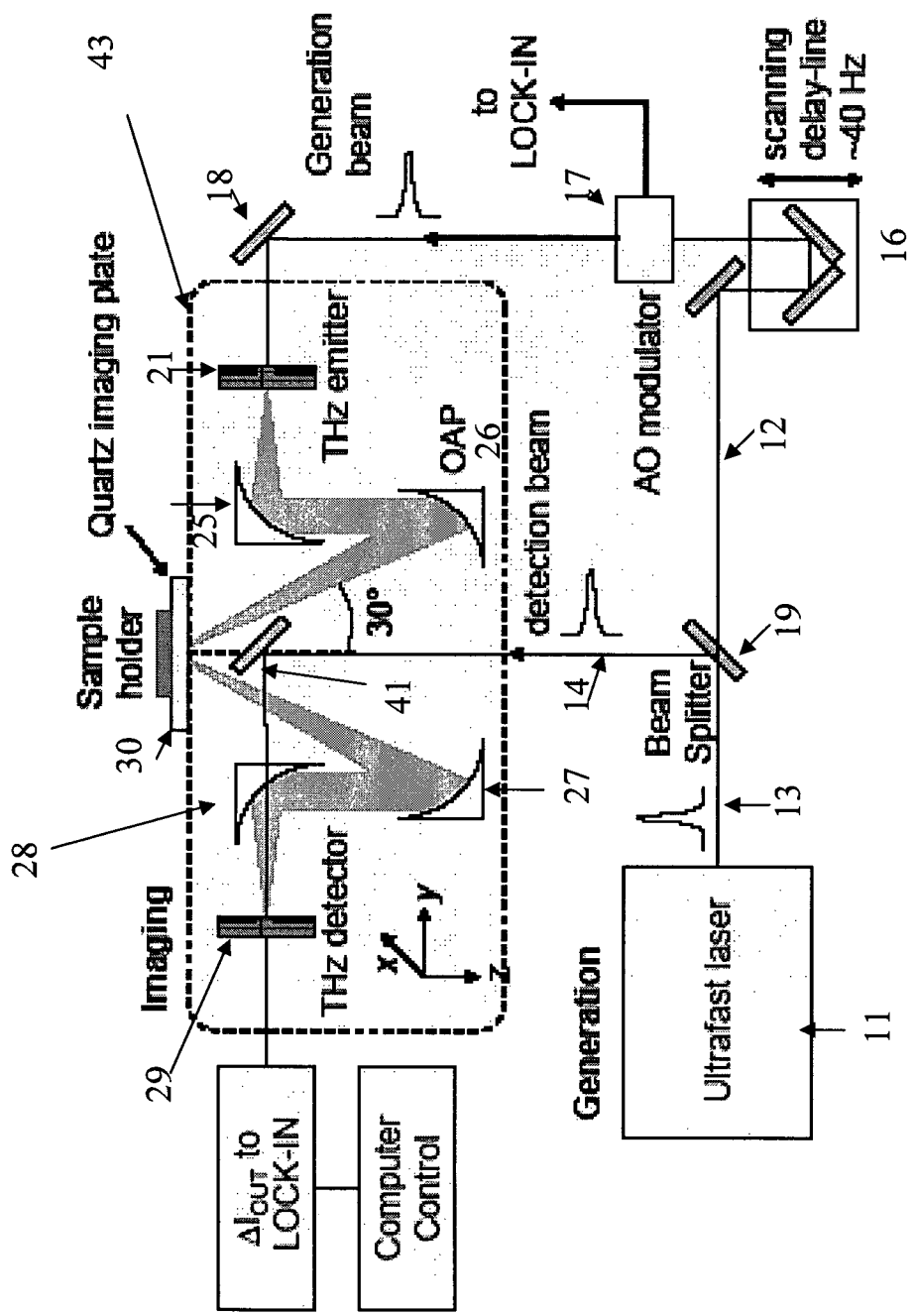
FIG. 1a is a schematic of a THz investigative system configured for reflection measurements.

FIG. 1a is a schematic of a terahertz imaging apparatus which may be used to study pharmaceutical tablets. The system shown is a flat bed scanner system. The apparatus comprises an ultra-short pulse laser 11 which may be, for example, Ti:sapphire, Yb:Er doped fibre, Cr:LiSAF, Yb:silica, Nd:YLF, Nd:Glass, Nd:YAG or Alexandrite laser. This laser 11 emits pulses of radiation 13, such as a collimated beam of pulses, each of which comprise a plurality of frequencies. This pulse impinges on beam splitter 19. The beam splitter splits the beam into a pump pulse 12 which is used to irradiate the sample and a probe pulse 14 which is used during detection.

The pump pulse 12 is directed into scanning delay line 16. This delay line is a rapid-scanning type and in its simplest form comprises two mirrors that serve to reflect the beam through a 180° angle. These mirrors are then quickly swept backwards and forwards in order to vary the path length of the pump pulse 12.

The output pump pulse from the scanning delay line 16 is then passed through AO modulator 17 which isolates the laser from reflected light and/or modulates the beam and directed by mirror 18 onto THz source 21. THz source 21 comprises a frequency conversion member and a bow-tie emitter. The frequency conversion member is configured to mix the incident radiation in order to output radiation derived from the differences of the input frequencies, so-called difference frequency generation. This technique is described in more detail in GB 2 347 835.

The emitter 21 abuts a hyper-hemispherical lens (not shown). The terahertz beam that is output from the emitter 21 is directed towards a first parabolic mirror 25. The beam is then reflected off the first parabolic mirror 25 and onto second parabolic mirror 26, which directs the radiation onto sample 30. The sample may be replaced with a reference sample in order to remove background features from the final results. The radiation which is reflected from sample 30 is then collected by third parabolic mirror 27 and directed onto a fourth parabolic mirror 28. Fourth parabolic mirror has a small aperture. The probe beam 14 is directed via mirror 41 through the aperture of fourth parabolic mirror 28 so that the probe beam can be combined with the radiation which has been reflected by the sample 30.

The combines THz radiation and probe beam then impinge on THz detector 29. In this particular embodiment, the THz detector is a photoconductive detector.

The components from the emitter 21, through the four parabolic mirrors and the detector 29 form the imaging section 43.

The sample introduces a time delay in the path of the pump pulse. The delay is dependent on both the absorption coefficient and the refractive index of the sample. In order to obtain a detection signal, the frequency component of the probe beam must be in phase with a frequency component of the pump beam. Variation of the scanning delay line allows the phase of the probe beam and/or pump beam to be swept with respect to the pump beam and/or probe beam and thus allows for measurement of the delay time of each frequency component which passes through the sample.

This apparatus described can be utilised to obtain time domain data of a sample using broadband phase-sensitive Terahertz radiation. To generate an image, measurements of the THz signal can be obtained from a number of different parts of the sample. For example the area of the sample which is to be imaged is subdivided into a two dimensional array of pixels and the reflected radiation from each of the pixels is detected. This provides depth information for each pixel.

In the apparatus of FIG. 1, the imaging section 43 moves to scan the radiation across the sample. Alternatively, the sample may be moved relative to the beam of radiation. Although a reflection system is described, it will be clear that the same principles may be applied to transmission systems where the detector 29 is provided on the opposite side of the sample to the emitter 21. Either the emitter and detector may be scanned together with a transmission system or, more conveniently, the sample is scanned in a transmission system.

Figure 1B:
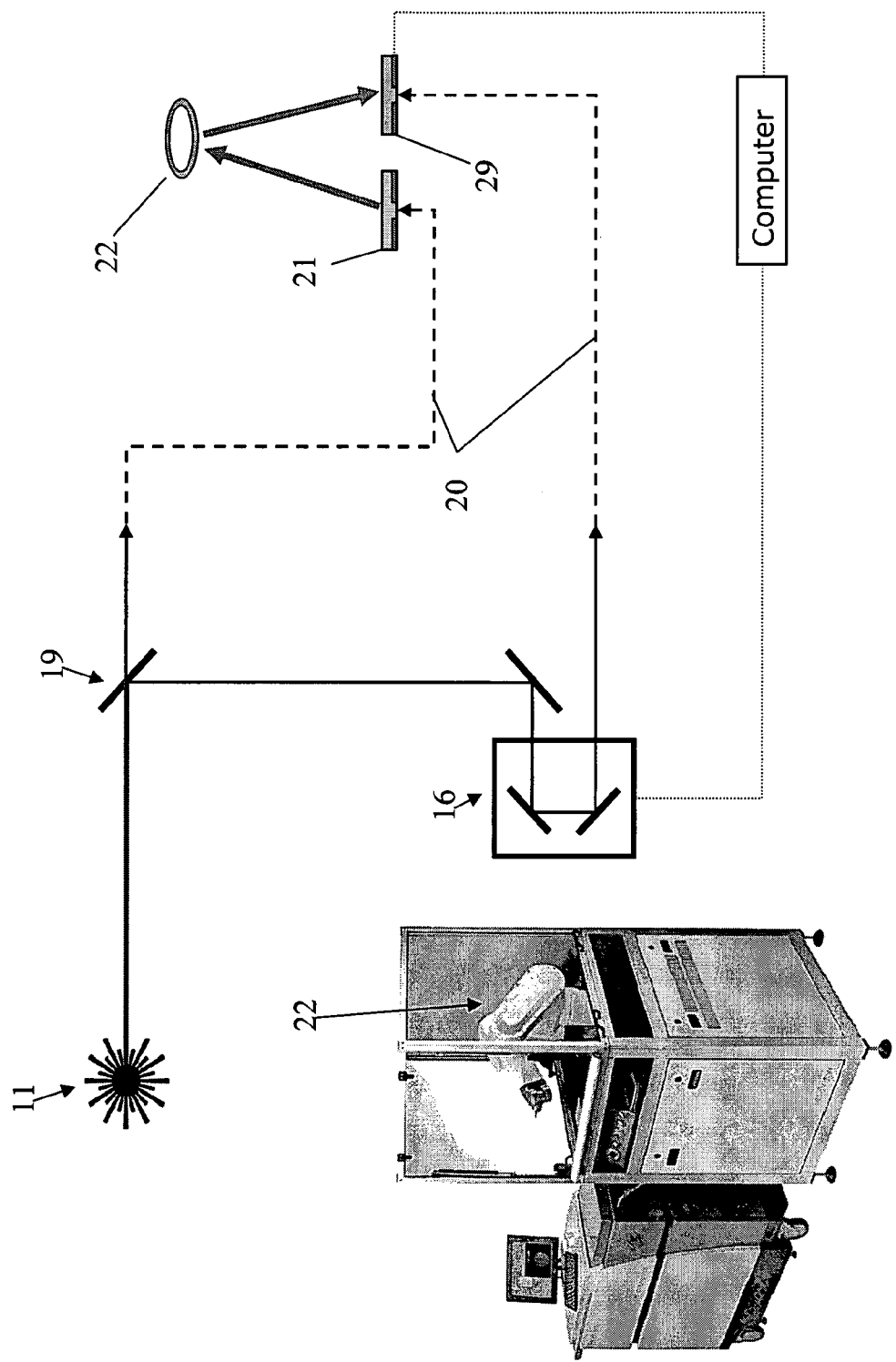
FIG. 1b is a schematic of a robot based THz investigative system.

FIG. 1b is a schematic of a variation on the imaging system of FIG. 1a. The system of FIG. 1b is based on that of FIG. 1a, but has a robotic arm and is fibre based. To avoid unnecessary repetition like features will be used to denote like features. Many of the mirrors of the system of FIG. 1a which are used to guide radiation to the emitter and detector are redundant in the design of FIG. 1b which uses optical fibres 20 to carry the probe pulse from delay line 16 to the detector 29 and to carry the pump pulse from beam splitter 19 to the emitter 21.

The sample is located on robot arm 22 which has movement along 6 axes. The robot arm 22 can be used to pick up and replace successive samples to allow tablets on a production line to be successively evaluated.

Terahertz imaging provides a purely non-destructive method of analysing pharmaceutical tablets.

Figure 2A:
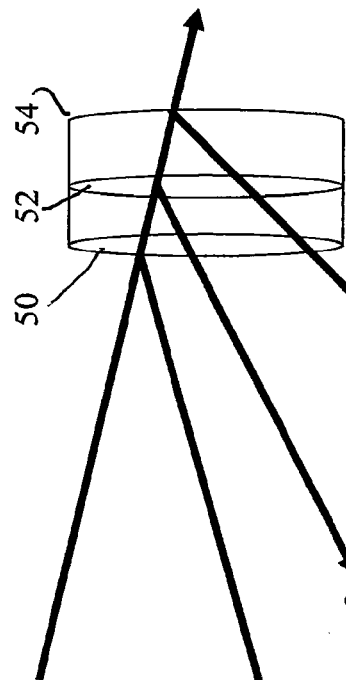
FIG. 2a is a schematic of a tablet with a buried interface and radiation being reflected from and transmitted through said tablet.
Figure 2B:
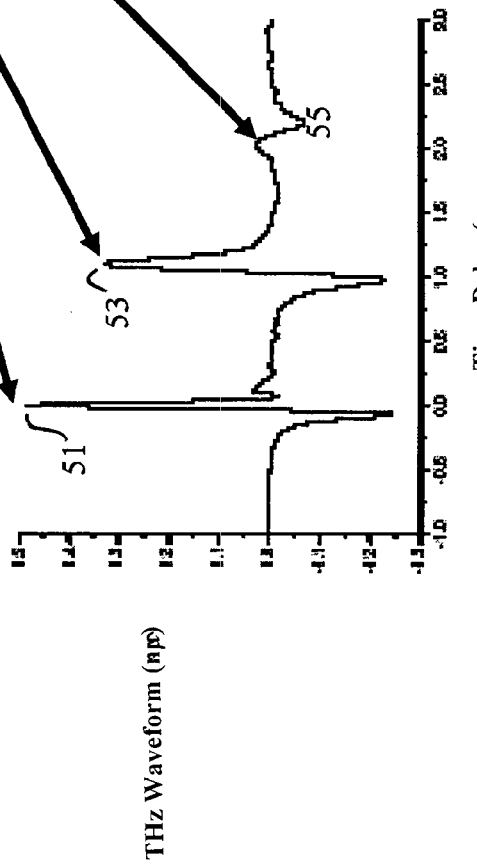
FIG. 2b shows a schematic THz reflection measurement of the tablet.

FIG. 2a is a schematic of a tablet with a first external interface 50, an internal interface 52 and a second external interface 54. Radiation which impinges of the tablet, is first reflected from the first external interface 50. This gives rise to large peak 51 in the reflected THz radiation spectra (FIG. 2b). Radiation which continues through the tablet is reflected from the internal interface 52 giving rise to peak 53 in the THz reflected time domain spectra (FIG. 2b). Finally, radiation which is transmitted through the internal interface 52 and reaches the second external interface 54 is partially reflected back through the tablet to form weak peak 55.

Generally, tablets would be measured through the back surface by turning the tablet around and measuring the interface from the other side.

By measuring the time at which the radiation is reflected from the tablet is possible to associate the measured radiation with different features within the tablet, thus it is possible to measure the thickness of certain layers within the tablet.

Figure 3:
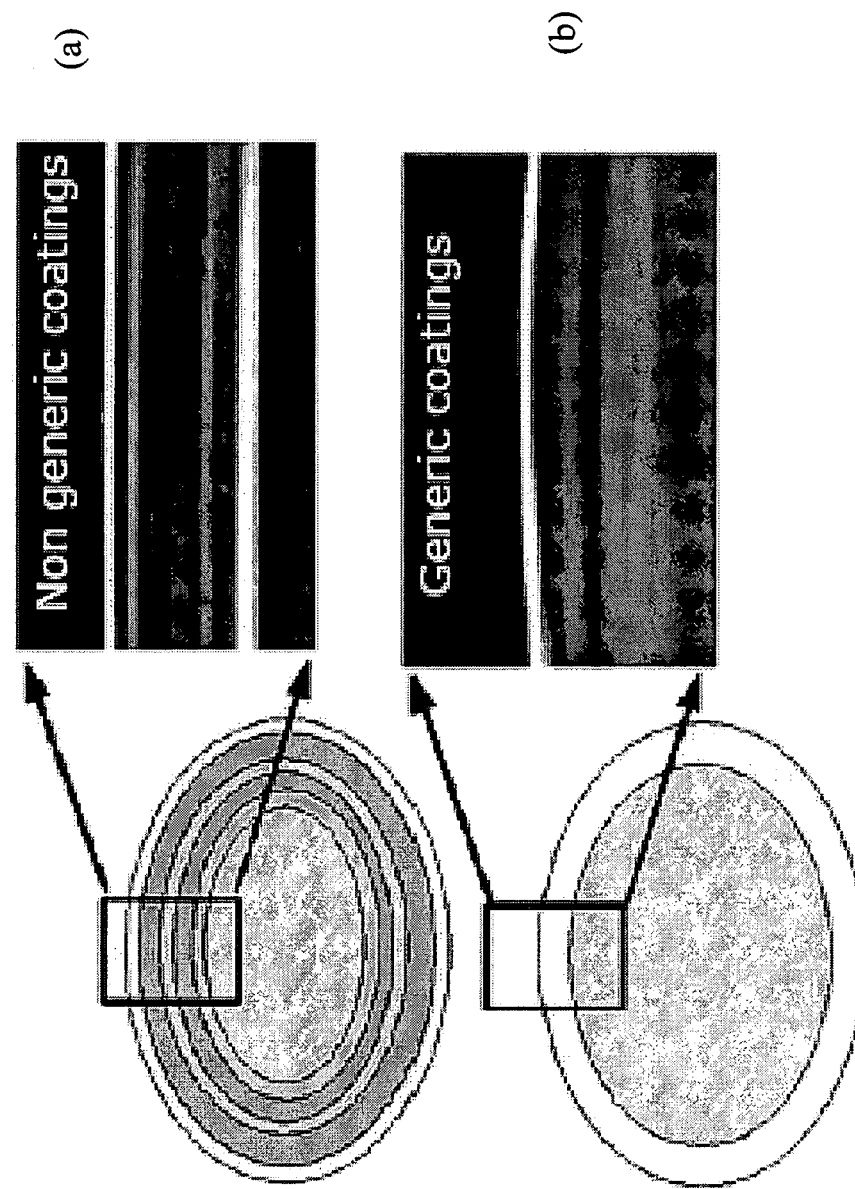
FIG. 3a is a schematic of a pharmaceutical tablet and its corresponding terahertz image and FIG. 3b is a diagram of the coating of a generic version of the pharmaceutical tablet of FIG. 3a and its corresponding terahertz image.

FIG. 3a is a schematic of a tablet with a reasonably complicated coating structure. The corresponding terahertz image of these coatings are shown to indicate the power of the terahertz analysis tool. FIG. 3b is a schematic of a generic form of the tablet of FIG. 3a. The terahertz analysis clearly shows a less complicated coating structure. Therefore, terahertz provides a way of distinguishing between generic and non-generic compounds, or possibly between counterfeit and authentic tablets or solid dosage forms in other contexts.

To demonstrate the effectiveness of using the apparatus described with reference to FIGS. 1a and 1b, two batches of the lab scale tablets were coated in a BFC5 (Bohle film Coater, pan diameter=316 mm, length=356 mm) and two batches of pilot scale tablets were coated in a BFC25 (pan diameter=546 mm and length=630 mm).

The coating parameters and the batch numbers are set out in table 1.

TABLE 1

| Process parameters | Batch numbers | | | | | | | | | |
|---|---|---|---|---|---|---|---|---|---|---|
| | Lab scale cBFC05_060718 cBFC05 060727 | | | | | Pilot scale cBFC25_060B09 cBFC25 050810 | | | | |
| | De-dusting | Pre-heating | Spraying | Drying | Cooling | De-dusting | Pre-heating | Spraying | Drying | Cooling |
| Pan speed [rpm] (on/off [5]) | 5 | 5 (30/30) | 20 | 12 | 10 | 3 | 3 (30/30) | 11.6 | 7 | 5.8 |
| Air volume [Nm³/h] | | 100 | 120 | 120 | 100 | | 545 | 720 | 545 | 545 |
| Negative pressure pan [Pa] | 200 | 30 | 30 | 30 | 30 | 200 | 30 | 30 | 30 | 30 |
| Outlet air temperature [0° C.] | | 45 | 40 | 60 | 30 | | 45 | 40 | 60 | 30 |
| Atomization air [mbar] | 1500 | | 1500 | | | 1500 | | 1500 | | |
| Pattern air [mbar] | 1800 | | 1800 | | | 1800 | | 1800 | | |
| Distance gun to tablet bed [cm] | 10 | | 10 | | | 10 | | 10 | | |
| Spray rate per gun [g/min] | | | 9 | | | | | 10.8 | | |
| No. of spray guns | | | 1 | | | | | 5 | | |

The geometric ratio between the two coating drums were the same. All four batches were coated with the same coating formulation onto tablet cores produced in the same fashion. For both scales two-way spray nozzles (type 970/7-1 S75) were used (Duesen-Schlick GmbH, Untersiemau/Coburg, Germany). One spray nozzle was used for the lab scale while five nozzles were used for the pilot scale.

The biconvex tablet cores consisted of 10% w/w of Diprophyllin (API), 5% w/w of Kollidon VA 64® (vinylpyrrolidone-vinyl acetate copolymer), 0.5% w/w of magnesium stearate and 84.5% w/w of Flowlac 100® (lactose monohydrate). All tablets were coated with the sustained-release coating formulation at 18 mg/cm².

The coating composition was as follows: 50% w/w Kollicoat SR 30 D® (polyvinyl acetate), 6% w/w Kollicoat IR (polyvinyl alcohol-polyethyleneglycol graft copolymer), 0.075% w/w Polysorbat 80® (polyoxyethylene (20) sorbitan monooleate), 0.3% w/w glycerolmonostearat, 0.75% w/w triethylcitrat and 42.87% w/w deionised water.

The geometry of a coated tablet was approximately 8 mm in diameter and 3 mm height. The coating process parameters were similar between the lab and pilot scales with variations in pan speed, air volume, spray rate per gun and the number of guns as shown in table 1.

For each pilot and lab scale batch, 100 tracer tablet cores were randomly mixed into the 20 kg pilot scale and 4 kg lab scale tablets before coating. These tracer tablets were weighed individually and marked using a permanent-marker with a cross on one side of the tablet surface and a number on the other side for identification. Once the tablets were coated with a transparent coating, all tracer tablets were subjected to a further drying step in the 60° C. chamber for 48 hours prior to weighing. Tablet coating weight gain for all tracer tablets was derived by subtracting the weight of the tablet core from the total weight of the respective tablets.

Ten tracer-samples were randomly selected from each batch and imaged using the apparatus of FIGS. 1a and 1b. Once the tablet was picked up by the robotic arm, the tablet was located at the 670 nm laser gauge. This directs a laser beam at the sample. The unit contains a feedback system which allows determination of the position of best focus. This corresponds to the tablet surface at the chosen tablet position. By moving the tablet position (i.e. by moving the robot) a model, the "morphological tablet model" of the shape of the tablet can be established. This is then used to ensure that the terahertz beam is correctly focused during subsequent terahertz scanning.

The tablets were examined using radiation in the THz frequency range of 60 GHz to about 3.6 THz. During terahertz scanning of a table there are a number of ways in which the robot moves in order to select points at which the terahertz signal is measured. One is the "trajectory mode". In this the tablet is scanned by requiring the robot to move in a series of orbits. For an elliptical tablet these orbits are themselves elliptical. Terahertz signals are acquired at (approximately) regular intervals as the robot traces the trajectory. On completion of each trajectory, the robot position then moves to the next (larger) trajectory and repeats until the tablet surface is completely scanned. Alternatively, the robot may be operated in "point to point" mode. Here, the surface is scanned in a step-wise manner. Points are chosen to be approximately equi-distant across a surface and the robot steps discretely from one point to the next. This is attractive because the inter-point distance can vary as little as possible. In this example, all terahertz scans were carried out in the point-to-point scan mode with 200 μm step size and a depth resolution of 38 μm.

The terahertz parameters measured were tablet coating layer thickness and peak signal strength. These parameters were determined separately for all three surfaces (top, bottom and central band). Unless stated otherwise, the average of the three surfaces was employed to simulate the complete coverage of all surface areas in the dissolution medium.

Coating layer thickness was yielded from the terahertz temporal waveform in the time domain. The time delay between the initial reflected signal off the tablet surface and the subsequent reflected signal from the interface between the coating matrix and the core constituted twice the coating layer thickness. Taking the refractive index of the coating structure into account, the coating layer thickness was derived by converting the time domain waveform into the depth domain (in μm) by multiplying by the speed of light.

$$2d_{coat} = \Delta t c/n.$$

where $d_{coat}$ is the coating layer thickness, $\Delta t$ is the time delay in the temporal waveform, c is the speed of light and n is the refractive index of the coating matrix.

The refractive index of the coating matrix was determined by measuring the surface reflectivity R of the signal off the coating structure. The reflectivity is the strength of the signal reflected from surface divided by the strength of the incident radiation signal.

$$R = (n_s - n_{air})/(n_s + n_{air}).$$

Where the surface refractive index is $n_s$, the refractive index of air is $n_{air}$. The surface refractive index is sensitive to surface roughness. However, by averaging the measured value over a plurality of points on the surface, it is possible to obtain an indication of the bulk refractive index.

Peak signal strength was calculated from the signal reflected off the coating surface normalised to the magnitude of the incident beam. This parameter was thus presented as a percentage. Moreover, multidimensional terahertz peak signal strength maps could be generated in the same fashion as the coating layer thickness maps.

Dissolution testing has long been employed by the pharmaceutical industry as the bench mark in evaluating the product quality and predicting in-vivo drug-release behaviour. Modelling of the dissolution rate for the modified-release dosage forms has proved to be relatively complicated when compared to the immediate release forms. Numerous dissolution rate models have been previously considered in an attempt to simulate the in-vivo performance; however none can accurately describe the drug-release behaviour. Nevertheless, there are model-independent dissolution parameters available and the following were used for the investigation of their correlation with the terahertz parameters:
mean dissolution time (MDT),
dissolution rate constant
dissolution times at $t_{20\%}$, $t_{50\%}$ and $t_{80\%}$ The Mean dissolution time was derived from:

$$MDT = \frac{\int_0^\infty t W_d(t) \cdot dt}{\int_0^\infty W_d(t) \cdot dt}$$

Where $W_d(t)$ is the cumulative amount of drug dissolved at any time interval

The dissolution rate constant is the gradient of the linear regression part of the dissolution curve from 0 to 180 minutes. $t_{20\%}$, $t_{50\%}$ and $t_{80\%}$ were also determined from the dissolution curve. These were derived from the time lapsed for the concentration of the drug release to reach 4, 10 and 16 mg respectively (total Diprophyllin in the tablet core=20 mg).

Non-directional independent t-tests were carried out on various dissolution parameters to demonstrate the functional behaviour between the lab and the pilot scales (on all four batches).

Instead of taking an average across two batches of the lab and two batches of the pilot scales, the following batch combinations were employed: cBFC25_060809 & cBFC05_060718, cBFC25_060809 & cBFC05_060727, cBFC25_060810 & cBFC05_060718, cBFC25_060810 & cBFC05_060727. This was done to ensure the variations investigated were solely attributed to inter-scale differences, circumventing any noise that arose from inter batch variations.

A summary of the results is shown in Table 2. The results showed that there were significant differences in the dissolution behaviour between the lab and pilot scales on all dissolution parameters examined (MDT, dissolution times at $t_{20\%}$, $t_{50\%}$ and $t_{80\%}$ and the dissolution rate constant).

It can be seen from the data that there is a significant difference between the data from the lab and pilot scales samples. All four batch combinations demonstrated significant product performance differences between the pilot and the lab scales, when model-independent dissolution parameters were employed as coating quality tests.

Figure 4:
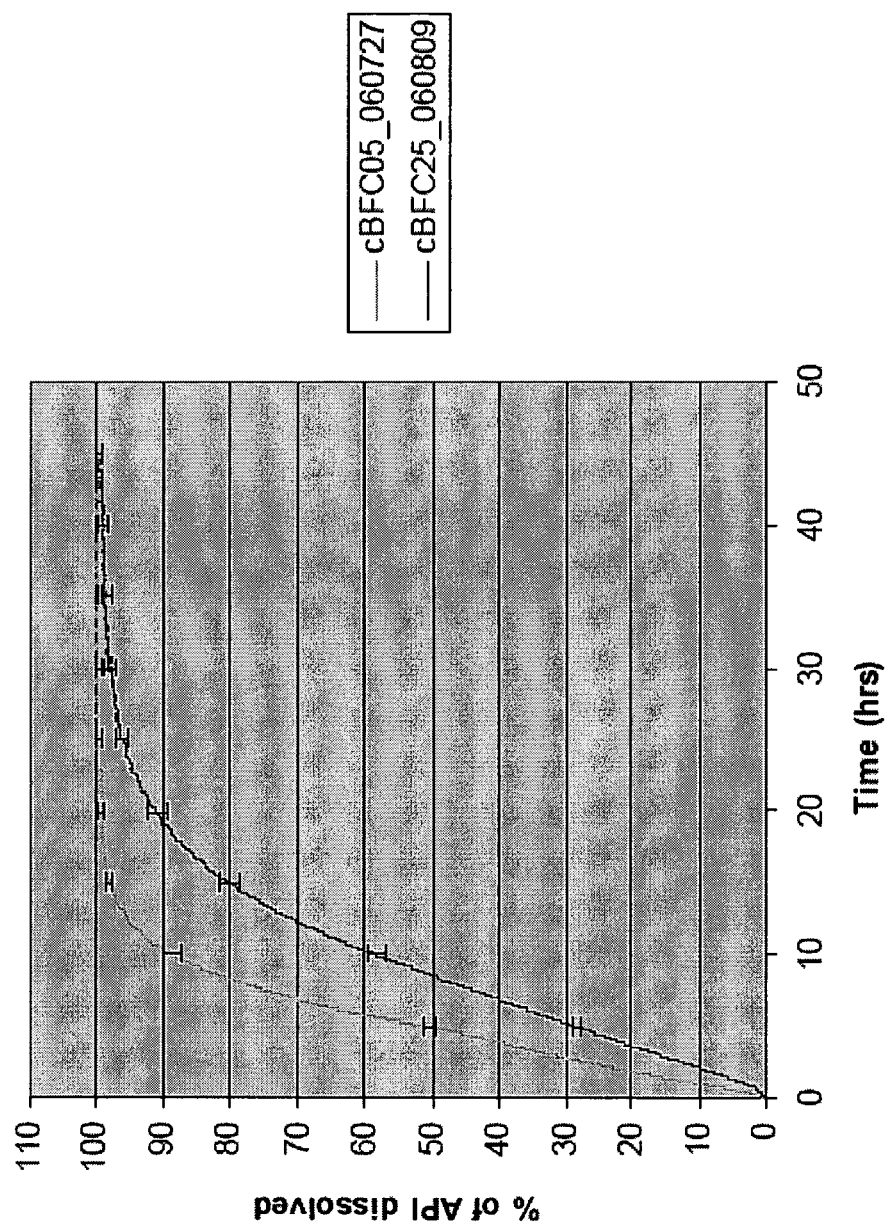
FIG. 4 shows the dissolution profiles of a batch of tablets prepared on a lab scale and a batch of tablets prepared on a pilot scale.

FIG. 4 is a plot of the % of API dissolved over time for lab-scale batch cBFC05_060727 and pilot scale batch cBFC25-060809. It can be seen that there are significant differences between the dissolution profile of the pilot scale batch and the lab scale batch. The lab scale batch dissolves far more quickly which shows that the lab scale tablets cannot be used to indicate the dissolution properties of the pilot scale tablets.

Using cBFC25_060809 & cBFC05_060727 as an example, the average MDT for cBFC2S_060809 (pilot scale, n=10) was 9.7 hours whereas the MDT for cBFC05_060727 (lab scale, n=9) was 5.4 hours. The MDT gives information on the in-vivo mean absorption time, which indicates that the absorption of diprophyllin from the lab scale is 44% faster than the pilot scale. This is shown in FIG. 4. This difference between the two scales was statistically significant at $\alpha=0.05$ ($P=1.0 \times 10^{-20}$).

The dissolution time for the API to reach 20, 50 and 80% of the total drug-release affords insight on the excretion of the drug into the urine in-vivo. When employed as dissolution coating quality parameters, all three time intervals indicated a much longer dissolution time for the pilot scale than that of the lab scale on all batches. The average $t_{50\%}$ for cBFC25_060809 was 8.6 hours for the pilot scale and 5.0 hours for the lab scale (cBFC05_060727). It thus took an additional 3.6 hours for the pilot scale to release half (10 mg) of the total API (20 mg). Other lab/pilot scale, batch combinations were all examined and showed similar trends (Table 2).

Overall, time-scale based parameters showed a prolonged dissolution profile for the pilot scale when compared to the lab scale.

The dissolution rate constant from the linear regression part of the dissolution profile (calculations based on the data collected from 0-3 hours) gives insight into the in-vivo drug absorption rate constant during the initial stage of the drug release prior to reaching the therapeutic level.

All other batches were also evaluated and results are displayed in Table 2. Even though the direction of the regression relationship is in reverse to that of the time-scale based dissolution parameters, the findings are in accordance that drug release from the lab scale tablets was faster than that of the pilot scale.

TABLE 2

|  | MDT (hr) | T20% (hr) | T½ (hr) | T80% (hr) | Dissolution release constant (mg/hr) | Weight gain (mg) | Peak signal strength (%) | Coating layer thickness (um) |
|---|---|---|---|---|---|---|---|---|
| 060809 Mean | 9.73 | 3.54 | 8.56 | 15.04 | 1.18 | 42.54 | 20.86 | 189.54 |
| 060810 Mean | 9.76 | 3.63 | 8.43 | 14.69 | 1.14 | 42.63 | 20.74 | 187.69 |
| 060718 Mean | 5.42 | 1.86 | 4.85 | 8.05 | 2.30 | 42.84 | 19.43 | 200.17 |
| 060727 Mean | 5.43 | 1.87 | 4.97 | 8.38 | 2.26 | 42.51 | 19.54 | 201.62 |
| 060809 & 060718 | | | | | | | | |
| SD | 2.22 | 0.87 | 1.91 | 3.62 | 0.58 | 0.49 | 0.81 | 6.02 |
| RSD % | 29.34 | 32.21 | 28.49 | 31.35 | 33.1i | 1.15 | 4.05 | 3.09 |
| T test | 2.0E−20 | 5.4E−20 | 5.1E−21 | 6.4E−17 | 3.7E−18 | 0.19 | 9.0E−08 | 4.1E−08 |
| 060809 & 060727 | | | | | | | | |
| SD | 2.21 | 0.86 | 1.85 | 3.44 | 0.55 | 0.74 | 0.77 | 7.10 |
| RSD % | 28.76 | 31.91 | 27.32 | 29.36 | 32.18 | 1.74 | 3.81 | 3.63 |
| T test | 1.01E−20 | 1.57E−21 | 7.15E−22 | 1.05E−18 | 5.12E−21 | 0.93 | 3.21E−07 | 5.08E−07 |
| 060810 & 060718 | | | | | | | | |
| SO | 2.25 | 0.91 | 1.84 | 3.45 | 0.60 | 0.39 | 0.74 | 6.72 |
| RSO | 29.71 | 33.31 | 27.77 | 30.38 | 34.77 | 0.91 | 3.70 | 3.47 |
| T test | 3.36E−16 | 6.20E−20 | 1.61E−20 | 1.47E−15 | 2.48E−18 | 0.25 | 5.37E−08 | 1.02E−10 |
| 060810 & 060727 | | | | | | | | |
| SO | 2.25 | 54.39 | 1.78 | 3.27 | 0.58 | 0.69 | 0.70 | 7.80 |
| RSD | 29.13 | 33.02 | 26.60 | 28.36 | 33.85 | 1.61 | 3.46 | 4.00 |
| T test | 1.36E−15 | 2.84E−21 | 2.70E−21 | 1.03E−16 | 4.67E−21 | 0.71 | 2.24E−07 | 1.28E−08 |

The weight gain for all tracer tablets was recorded and the results are shown in table 2. The relative standard deviation of 1.74% indicated low variation in weight gain between the two scales. This implies that tablet weight gain as a sole coating quality parameter is insufficient for the prediction of the dissolution/functional performance of the sustained-release products examined.

In contrast to weight gain, results from both terahertz parameters of peak signal strength and coating layer thickness are in agreement with the bench-mark dissolution parameters. In this way, the functional performance differences can be distinguished between the two scales. All batches were examined though cBFC25_060810 (pilot) and cBFC05_060718 (lab) were used to describe the relationships between the pilot and the lab scales. The derived average terahertz peak signal strength for the lab scale was 19.4% whilst 20.7% was derived for the pilot scale, with a relative standard deviation around 3.7%. This is in contrast to the 0.9% relative standard deviation calculated for the weight gain. The average coating layer thickness for the lab batch was 12 μm thicker than the pilot scale with an average thickness around 200 μm. A variation was observed of around 6% between cBFC25_060810 (pilot) and cBFC05_060718 (lab) and a relative standard deviation of 3.5%.

In general, applications of the terahertz parameters to the coating scale-up process (for assessing the coating quality in the dry-state), gave better reflection of the true functional performance than that of weight gain.

The correlation coefficient (R) was calculated using linear regression to investigate the relationship between the model-independent dissolution parameters and terahertz parameters. This was compared to the dissolution correlation to the tablet weight gain. To avoid inter-batch coating variations interfering with the data analysis, coating parameter correlations were carried out systematically on the following batch combinations: cBFC25_060809 & cBFC05_060718, cBFC25_060809 & cBFC05_060727, cBFC25 060810 & cBFC05_060718, cBFC25_060810 & cBFC05_060727.

Using the batch combination cBFC25_060810 & cBFC05_060718 as an example, correlation coefficient (R) of MDT and both terahertz parameters were generated. The correlation coefficient of peak signal strength was 0.89 and coating layer thickness was −0.95. This indicates that the direction of the correlation for the peak signal strength with the MDT was the reverse to the relationship exhibited by the coating layer thickness as a parameter.

The coefficient of determination ($R^2$) was also generated to express the relationship between all the coating quality parameters. FIG. 5a is a plot showing the correlation between the MDT for tablet batches cBFC25_060810 & cBFC05_060718 and the weight gain of tablets during the coating process; FIG. 5b is a plot showing the correlation between MDT and the thickness of the coating layer; and FIG. 5c is a plot showing the correlation between the MDT and the maximum strength of the reflected THz signal.

Values of 0.79 and 0.90 were derived for the correlation between MDT to the peak signal strength and coating layer thickness respectively. These depicted that the 79% and 90% of the MDT dissolution behaviour could be explained by terahertz parameters. All correlations with terahertz parameters were at least 8 times stronger than the correlation between MDT and weight gain ($R^2$=0.09), with the coating layer thickness being 10 times stronger.

All other three batch combinations (cBFC25 060809 & cBFC05 060718, cBFC25 060809 & cBFC05 060727, cBFC25_060810 & cBFC05_060727) showed similar trends—that the three terahertz parameters had a much more robust correlation to the MDT than when weight gain was employed as dry-state coating quality parameters.

Time interval dissolution parameters at various target drug-release concentrations (20%, 50% and 80%) were also investigated for their relationship with terahertz coating parameters. Similar to the relationships depicted by the MDT, batch cBFC25_060810 & cBFC05_060718 returned correlation coefficients in the positive direction with terahertz peak signal strength. The correlation with coating layer thickness was also strong though in the negative direction. From these results it can be derived that the thicker the average coating layer thickness, the shorter the dissolution time-interval for each of the target drug-release concentrations.

All coefficients of determination values for cBFC25_060810 & cBFC05_060718 are presented in Table 3. Both of the terahertz parameters show a robust correlation to various target-release concentration time intervals when compared to the weight gain alone as the dry-state coating quality parameter.

The explanation lies in the fact that the sustained-release coating used in this study is an insoluble matrix with pore formers. The dissolution of such a tablet is shown in FIGS. 7a (2.5 hours), 7b (4.5 hours), 7c (5.5 hours) and 7d (7 hours). The tablet can be seen to expand as dissolution progresses.

During dissolution, the medium penetrates and dissolves the hydrophilic pore formers (polyvinyl alcohol-polyethyleneglycol graft copolymer) in the hydrophobic (polyvinyl acetate) coating matrix before it reaches the tablet core. The

TABLE 3

| | MDT | T20% | T50% | T80% | release constant 060810&060718 | Weight gain | peak signal strength | Coating layer thickness |
|---|---|---|---|---|---|---|---|---|
| Correlation coefficient MDT | 1.00 | 0.99 | 0.99 | 0.99 | −0.98 | −0.29 | 0.89 | −0.95 |
| Correlation coefficient T20% | 0.99 | 1.00 | 1.00 | 0.99 | −1.00 | −0.24 | 0.90 | −0.93 |
| Correlation coefficient T½ | 0.99 | 1.00 | 1.00 | 1.00 | −1.00 | −0.27 | 0.90 | −0.94 |
| Correlation coefficient T80% | 0.99 | 0.99 | 1.00 | 1.00 | −0.99 | −0.26 | 0.90 | −0.93 |
| Correlation coefficient Release constant | −0.98 | −1.00 | −1.00 | −0.99 | 1.00 | 0.24 | −0.90 | 0.93 |
| $R^2$ MDT | 1.00 | 0.97 | 0.98 | 0.98 | 0.97 | 0.09 | 0.79 | 0.90 |
| $R^2$ $t_{20\%}$ | 0.97 | 1.00 | 1.00 | 0.98 | 1.00 | 0.06 | 0.80 | 0.87 |
| $R^2$ $t_{50\%}$ | 0.98 | 1.00 | 1.00 | 0.99 | 1.00 | 0.07 | 0.81 | 0.89 |
| $R^2$ $t_{80\%}$ | 0.98 | 0.98 | 0.99 | 1.00 | 0.99 | 0.07 | 0.80 | 0.86 |
| $R^2$ Release constant | 0.97 | 1.00 | 1.00 | 0.99 | 1.00 | 0.06 | 0.81 | 0.86 |

The dissolution release constant for the linear regression part of the dissolution profile (time interval 0-3 hours) was investigated for a relationship with the dry-state coating quality parameters.

FIG. 6a is a plot showing the correlation between the release constant for tablet batches cBFC25_060810 & cBFC05_060718 and the weight gain of tablets during the coating process; FIG. 6b is a plot showing the correlation between the release constant and the thickness of the coating layer; and FIG. 6c is a plot showing the correlation between the release constant and the maximum strength of the reflected THz signal.

The terahertz peak signal strength displayed a negative relationship when correlated to the dissolution release constant. The coating layer thickness showed a positive correlation coefficient (0.93), indicating that the thicker the coating layer the faster the dissolution rate. Despite the direction of the relationships being reverse to the time-interval based dissolution parameters (MDT and $t_{50\%}$), the underlying relationships with the dry-state quality parameters were the same. Once again, both terahertz parameters yield an $R^2$ value much higher than that of the weight gain when correlated to the release constant.

Correlating terahertz parameters to the dissolution coating quality parameters discussed previously has resulted in certain observations. The thicker the coating layer, the faster the dissolution rate and the duration of dissolution for the MDT and dissolution times at $t_{20\%}$, $t_{50\%}$ and $t_{80\%}$ were shorter. This contradicts common knowledge of drug-release profiles that the thinner the coating thickness, the faster the dissolution rate.

initial linear cumulative drug-release represents the lag-period of the drug dissolution before steady-state is being reached. Once the number of pores is established and the osmotic pressure inside the tablet-core reservoir is stabilised, then constant drug release can be realised within the therapeutic range. The dissolution rate of this drug release is subsequently governed by the transportation of the drug through the pores by the medium. This dissolution behaviour has been described by:

$$M_t = A\left[\frac{D\varepsilon C_s t}{\tau}(2C_0 - \varepsilon C_s)\right]^{0.5}$$

Where $M_t$ is the amount of active drug released at time (t) and A is the surface area of the solid dosage form. D is the diffusion coefficient, $C_s$ is the solubility of the drug in the medium through the porous structures, and $C_0$ is the loading dose. The symbol $\varepsilon$ represents the porosity of the coating matrix and the tortuosity ($\tau$) of the pores is also taken into account. From this equation, the degree of drug release is directly proportional to the porosity the coating matrix. This concurs with our findings with terahertz parameters.

The Terahertz electric field peak strength (TEFPS) exhibited positive correlations with the MDT, dissolution times at $t_{20\%}$, $t_{50\%}$ and $t_{80\%}$. This inverse correlation pattern in comparison to coating layer thickness indicates the existence of an intrinsic physical property. Both terahertz peak signal strength and coating layer thickness are strongly influenced by the refractive index. Whilst the refractive index used to derive an accurate coating layer thickness is material dependent, variations in the TEFPS are dependent on the refractive index of the coating surface. The surface reflectivity of the signal off the coating structure (represented directly through the TEFPS) is related to the surface refractive index ($n_s$) by: $R=(n_s-n_{air})/(n_s+n_{air})$. This surface dependent refractive index shares the same inherent physical-chemical properties as the material dependent refractive index. However, the surface dependent refractive index is somewhat sensitive to signal scattering due to intrinsic surface coating roughness. This property affords TPI an ideal tool to detect subtle orange peel defects on the coating structure.

For the purpose of correlation regarding the terahertz peak signal strength to the dissolution parameters, it was observed that subtle changes in the visible surface roughness on some tablets (visible in peak signal strength 2D terahertz maps) did not constitute a significant variations in the signal strength reflected back from the surface of the tablet coat. The terahertz peak signal strength value used in this study is derived from an average of 4000 pixels over the whole tablet surface, hence subtle changes in some of these pixels did not affect the average TEFPS.

In this study, the chemical properties of the refractive index were controlled during the scale-up process as the relative quantity, volume and the composition for the coating formulation were exactly the same for both scales leaving the physical properties governing the changes in the refractive index. Since density of the coating structure is the major contributor to the changes in the observed refractive index and hence changes in peak signal strength, it may have the potential to be employed to predict the dissolution behaviour of the sustained-release coated tablets with an insoluble matrix. Not only is this supported by the dissolution behaviour of the tablets examined with peak signal strength, but it also corresponds to the dissolution correlation behaviour with the coating layer thickness as a dry-state coating quality parameter. The coating layer thickness for the pilot scale were thinner (higher coating density) than that of the lab scale, indicating lower porosity in the coating matrix.

Since the dissolution behaviour of the sustained release tablets is directly related to the porosity of the structure concerned, one would expect a relatively longer dissolution profile and slower dissolution rate for the pilot scale. Indeed this was observed with the correlation behaviour between the dissolution profiles and coating layer thickness derived from the terahertz measurements.

During the course of the data analysis inter-batch variations became apparent within each of the scales, thus all coating quality parameters were examined with most of the coating parameters showing statistically in-significant differences between the batches within each of the scales (Table 4).

However, the dissolution rate constant and $t_{20\%}$ measured between the two batches for the pilot scale (cBFC25_060810 and cBFC25_060809) showed a significant difference. The average drug release rate constant derived during the first three hours was 1.18 mg/hr for cBFC25_060809 and 1.14 mg/hr for cBFC25_060810. The relative standard deviation of 2.25% was deemed a significant inter-batch variation for the pilot scale at P=0.02 (a=0.05).

When $t_{20\%}$ was employed as a dissolution parameter, cBFC25_060809 was 5 minutes faster than cBFC25_060810 to release 4 mg out of the total drug reservoir of 20 mg. This yielded a relative standard deviation of 1.68%. Compared to the pilot scale, both batches of the lab scale tablets investigated indicated no major inter-batch variations on all coating parameters examined.

The results of interbatch variations are shown in FIG. 8. Where the relative standard deviation is plotted for both lab scale and pilot scale tablet batches.

FIG. 9 is a plot of coating thickness against the terahertz electric field peak strength (TEFPS) for a plurality of coating films of different weights for tablets. The weights are shown in the key. Hollow symbols correspond to tablets fabricated using pilot scale techniques and solid symbols correspond to lab scale tablet coating methods.

The terahertz electric field strength is measured as the reflected terahertz signal from the external interface expressed as a percentage of the reflective terahertz signal from a mirror.

It can be seen that coating films of a similar weight vary in thickness and hence density, a lower TEFPS signal indicates a lower refractive index which indicates a lower coating density. As previously explained, a lower coating density indicates a shorter dissolution time.

FIG. 10 is a plot of the terahertz electric field strength (expressed as a percentage of the signal from a perfect reflector) against mean dissolution time (MDT) in hours. Data is shown from both lab scale fabrication techniques of the tablets and pilot scale fabrication techniques. The different coating weights are shown in the key.

It can be noted that although samples from both pilot scale and lab scale have relatively similar polymer weight gains during the coating process (as shown by the key), samples from the pilot scale display a much longer MDT than those of the lab scale. The TEFPS signal for the coatings formed by lab scale methods were lower than those for the pilot scale methods. Lower TEFPS values indicate a lower coating density which was confirmed with a shorter MDT for the lab scale.

FIG. 11 is a plot of coating thickness against MDT for lab and pilot scale fabricated tablets. The coating weight is shown

TABLE 4

|  | Weight. gain | MDT (hr) | $t_{20\%}$ (hr) | $t_{50\%}$ (hr) | $t_{80\%}$ {hr} | Release constant (mg/hr) | Peak signal strength | Coating layer thickness |
|---|---|---|---|---|---|---|---|---|
| Lab scale mean | 42.67 | 5.42 | 1.66 | 4.91 | 8.21 | 2.28 | 19.49 | 200.90 |
| SD | 0.23 | 0.01 | 0.01 | 0.08 | 0.23 | 0.03 | 0.07 | 1.03 |
| RSD % | 0.54 | 0.16 | 0.38 | 1.71 | 2.83 | 1.24 | 0.38 | 0.51 |
| T test | 0.35 | 0.97 | 0.85 | 0.13 | 0.13 | 0.36 | 0.57 | 0.36 |
| Pilot scale mean | 42.59 | 9.75 | 3.58 | 8.49 | 14.86 | 1.16 | 20.80 | 188.61 |
| SD | 0.06 | 0.02 | 0.06 | 0.09 | 0.25 | 0.03 | 0.06 | 1.31 |
| RSD % | 0.15 | 0.21 | 1.68 | 1.08 | 1.65 | 2.56 | 0.39 | 0.70 |
| T test | 0.66 | 0.85 | 0.02 | 0.17 | 0.27 | 0.02 | 0.41 | 0.05 | in the key. As for FIG. 10, it can be seen that the MDT for the lab scale is shorter than that of the pilot scale.

FIG. 12a is a plot of the terahertz electric field strength in the time domain from the top and bottom surfaces of a tablet. The tablet here is a sustained release coated tablet. The peak due to the terahertz being reflected from the external surface between the air and the coating is indicated by line 1 and the peak or dip (as in this case) of the reflection from the interface between the coating and the core is shown as line 2.

FIG. 12b again shows a terahertz time domain trace from the same tablet, but this time, the data is taken from the central band.

It can be see in FIG. 12a that there is a negative peak from the interface between the coating and the core which indicates that the refractive index of the coating is larger than the refractive index of the core. However, FIG. 12b shows that for the same tablet, when the measurement performed at the central band, there is a positive peak in reflection from the coating/core interface would suggest that the refractive index of the coating is smaller than that of the core.

Since the refractive index for the core will be the same regardless of whether the measurement is taken at the central band or on one of the top or bottom surfaces, this indicates that the coating refractive index is changing between the central band and the top and bottom surfaces. Actually, it shows that the refractive index of the central band is lower than the refractive index of the coating on the top and bottom interfaces.

Thus, the film coating density of the central band is lower than on the top and bottom surfaces. This suggests that the central band is the weakest point during drug dissolution and that Terahertz measurements should be made of the central band.

A useful parameter to measure is the terahertz interface index. The terahertz interface index is the percentage of the peak reflected from the coating/core interface over the peak reflected from the air/core interface. The top and bottom surfaces, the terahertz interface index was found to vary from 2.5 to 4.5. This is in contrast with the central band where the interface index varied from 0.6 to 2.2.

The same tablets, the TEFPS signal was found to range from 19.21 to 20.66 for top and bottom surface and from 16.77 to 19.88 for the central band. As a central band is curved, the TEFPS signal can be degraded to scattering around the central band. The terahertz interface index measurement corrects for this scattering.

TABLE 5

| 3 Surfaces | Pilot scale | $R^2 = 0.91$ | RMSE = 12.81 |
| | Lab scale | $R^2 = 0.88$ | RMSE = 16.24 |
| Central Band | Pilot scale | $R^2 = 0.92$ | RMSE = 8.41 |
| | Lab scale | $R^2 = 0.88$ | RMSE = 11.03 |
| Top & Bottom | Pilot scale | $R^2 = 0.90$ | RMSE = 15.22 |
| | Lab scale | $R^2 = 0.88$ | RMSE = 18.98 |

Table 5 shows results from the MDT compared with the terahertz parameters for the central band. It can be seen that better correlation data is seen for the central band in the RMSE (root mean square error) value.

FIG. 13a shows a SEM image taken from the top or bottom surfaces of a sustained-related tablet. The surface seems to be smooth at a magnification of 40×. FIG. 13b shows the SEM image taken form the central band. It can be seen that the surface is rough with golf-ball like features possibly from coating solution droplets. The SEM pictures therefore show that the surface roughness on the central band is much more distinct than on the top and bottom surfaces. Therefore, the surface area in contact with the dissolution medium of the central band is much larger than on the top or bottom surfaces.

The SEM images support the terahertz analysis view that the central band is the weak point of the tablet.

FIGS. 14a and 14b are images which show how further information about the dissolution profiles of tablets may be derived using non-destructive terahertz testing. The image in FIG. 14a is constructed by obtaining the interface index for a plurality of points across a sample as described with reference to FIG. 2.

The tablet imaged in FIG. 14a and FIG. 14b has a groove across the centre of the tablet to allow easy breaking. This feature can be clearly seen in the images. FIGS. 14a and 14b are taken from different tablets of the same sample. Although the composition of the tablets is the same, they have been manufactures using different process parameters or conditions. The images are taken using radiation which arises from reflections 1 mm below the surface of the tablet. The images can be seen to differ significantly indicating that the two samples although measured under exactly the same conditions have considerably different dissolution characteristics.

It can be seen that the plot of FIG. 14a the amplitude of the reflected signal across the tablet appears to be higher than that of FIG. 14b, and that there are different features in the two images. These are indications that the dissolution properties are better for the tablet of FIG. 14a.

FIGS. 15a and 15b also show terahertz images obtained by plotting the interface index for radiation which has been reflected from a specific depth below the surface for two tablets taken from different batches. The differences in the images are seen to correspond to different dissolution properties of the tablet (acceptable vs. unacceptable dissolution rates for tablets 15a and 15b respectively), and as such THz images have the potential to be used to determine the dissolution by non destructive means.

The coating thickness of a tablet is also related to dissolution. FIG. 16 shows a plot of the onset of dissolution in minutes against the mean thickness of a coating in microns. The mean thickness was measured using terahertz radiation on one facet of a tablet. Tablets from three groups were chosen, group 1, group 2 and group 3. It can be seen that in all cases, the onset of dissolution increases with coating thickness. A mean coating thickness of 70 μm or more tends to result in an onset of dissolution after 2 hours i.e. 120 minutes.

Figure 17:
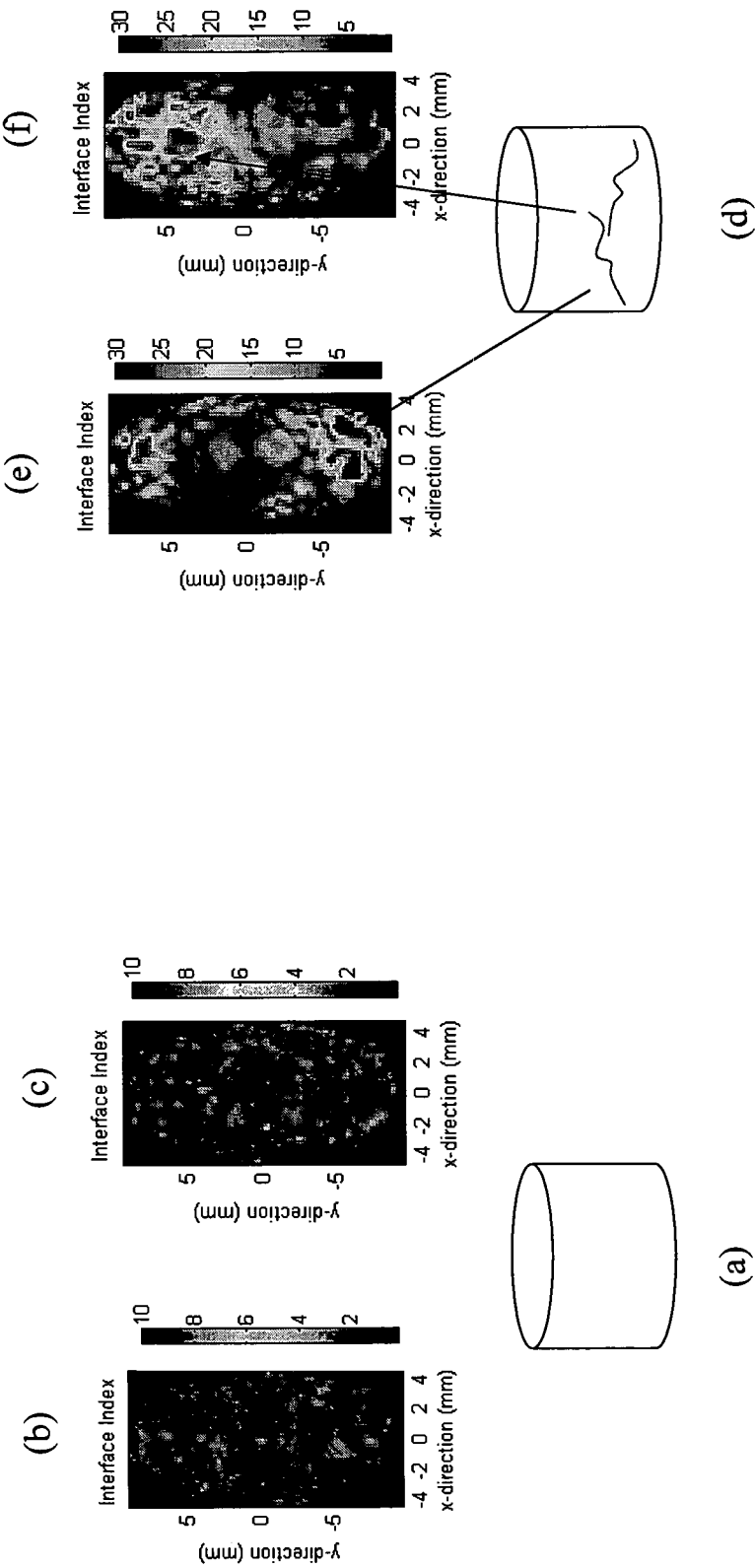

FIG. 17 shows images concerned with delamination and capping in tablets. FIG. 17a is a schematic of a theoretically perfect tablet with no cracks.

FIG. 17d is a schematic of a poor tablet with deep cracks which are invisible to the eye. The two tablets (FIGS. 17a and 17d) are intended to be chemically identical. However, due to variations in manufacture, for example, tablet press parameters (compression force, speed) the tablet of FIG. 17d is much poorer than that of FIG. 17a.

FIGS. 17b and 17c are plots of the interface index for two different tablets. The interface index is determined as explained with reference to FIG. 2. In the images of FIGS. 17b and 17c, the interface index at different depths is plotted on a 2D surface to give an indication of what regions of the tablet have cracks or dislocations and which do not. In this particular example, a measurement of the interface index through the sample is performed for each point in a plane through the sample. The maximum interface index then calculated for each point through the sample is plotted.

FIGS. 17e and 17f similarly plot the interface index. As can be seen, there are significant differences between the tablets (a) and tablets (d) prepared using different compression parameters.

In contrast, the images of FIGS. 17e and f which were obtained using the same method as described with reference to FIGS. 17b and 17c show the presence of cracks which are highlighted in the figures. These cracks indicate that delamination is likely to occur which will ruin the properties of the tablet, resulting in delamination (splitting) of the tablets and/or failure of dissolution tests, etc.

FIGS. 18a and 18b show slices in depth through a tablet. The first tablet is subjected to a compression force of 40 kN at a rate of A plurality of images are generated using radiation measured at different delay times and hence different penetration depths. Thus, it can be thought that the tablet has been sliced using terahertz images. The images show a fairly uniform block of colour.

FIG. 18b shows a tablet of the same composition but manufactured using different parameters. This tablet was subjected to a compression of 60 kN. Again, a plurality of terahertz images of the interface index for different depths is shown. Comparing the images of FIG. 18b with that of FIG. 18a, it can be seen that the images of FIG. 18a are generally uniform where as many of the images of FIG. 18b have sharp features. These sharp features indicate the presence of large internal cracks and show that the tablet of the FIG. 18b is of poorer quality and will suffer from delamination and capping.

The identification of features as cracks, dislocations or delamination can be further confirmed by examining the time domain and/or spectral waveforms, which will show characteristics of waveforms associated with small air gaps or related features in the tablet matrix.

When studying delamination, it is useful to look at the terahertz signature from a buried interface. Many tablets are fabricated by compressing two powders together. In this particular example, FIG. 19a shows a layer of a first formulation (excipient and/or API) 201 overlying a layer of second formulation 203. The two layers are joined to form buried interface 205. Two batches of tablets were manufactured.

In batch 1, three tablets were studied and the interface index was measured at the depth of the buried interface. In FIGS. 19b, 19c and 19d, the interface indexes found to vary by less 30% and this is known to be a small enough variation to avoid delamination. In FIGS. 19e, f and g, tablets from a second batch are measured. Here, it was found that there was an unacceptable variation in the interface index of 150%. These tablets were known to suffer from compression difficulties and delamination.

FIG. 20a is a schematic of hydroxypropyl methyl cellulose (HPMC) matrix. A 10 µl drop of water 501 is placed on an HPMC matrix 503. The water will diffuse into the HPMC matrix 503. The figures of 20b show vertical cross-sections in the direction of lines 507 through matrix 503.

The vertical cross-sections are obtained by measuring the time domain reflected terahertz spectra for a line across the surface of the matrix. The lines along which the terahertz spectra are taken start at points 507, 509 etc and travel into the plane of the page.

The technique demonstrates a non-destructive way of assessing water ingression into a sample. The images were taken from left to right across the matrix, with the image at the top left (i) representing the first image. It can be seen that in image (vi) the straight profile of the surface of the top of the matrix is perturbed in the centre of the image. This perturbation gets stronger and stronger as the images slice through the area of the matrix and the drop 501. It can be seen that when slice (xvii) is reached, the surface returns to being flat and no evidence of the water drop is observed.

FIG. 21a again shows a water droplet 501 on a HPMC matrix 503. This time, instead of vertical slices through the HPMC matrix, horizontal slices are shown. This data may be achieved by scanning the whole of the top surface of the HMPC matrix and extracting the time domain spectra in reflection for specific delay times.

The images shown in FIG. 21b show a plot of the refractive index profile obtained at delay times that correspond to 40 µm spaced slices. In the first and top most image the water drop 501 can be clearly seen. As slices are taken deeper and deeper into the matrix, the contrast in the image due to water drop 501 is seen to decrease. However, even in the final image, the signature of the water drop 501 can still be seen indicating that the water drop has penetrated this far into the structure.

The refractive index is derived from amplitude of the pulse compared to that for the matrix and known materials used. Although the refractive index is used here, it is also possible to use the interface index or other parameters to monitor ingression and plot out the water profile;

FIG. 21c is based on the data of FIG. 21b. However, it shows the change in refractive index which shows the effect of drop 501 on the matrix in even more contrast. The change in refractive index due to water is measured with respect to the refractive index of the surrounding HPMC matrix.

FIG. 22a is a schematic of a cross-section of a tablet. A schematic of a tablet is shown in FIG. 22b. A point 301 where the measurement is made is shown on FIG. 22b.

The cross-section of FIG. 22a is a schematic of a cross-section through point 301. The cross-section first shows a seal coating 303. This is formed overlying the sustained release (SR) coating 305. The SR coating overlies the tablet core 307. It should be noted that only half of the tablet is shown. Of course, the tablet core is fully surrounded by the SR coating 305 and seal coating 303.

FIG. 22c shows a plot of the reflected signal intensity over time, which is also equivalent to depth inside the tablet below the tablet surface. First, the reflection from the outer interface 303 is seen. Next, smaller peaks due to the interface between the seal coating and the SR coating and the SR coating and the tablet core are observed. Then, there is a sharp decrease in the signal and then a gradual rise to the constant signal for the tablet core. This sharp decrease is due to the presence of a compound which is a strong absorber of terahertz radiation. Water is a known absorber of terahertz radiation. Therefore, this technique can be used to examine water ingression in tablets. The characteristic slow rise of the signal back to the baseline (0) between ~0.3 and 0.6 mm is characteristic of a strongly absorbing, highly dispersive medium in the THz, such as water.

Figure 22:
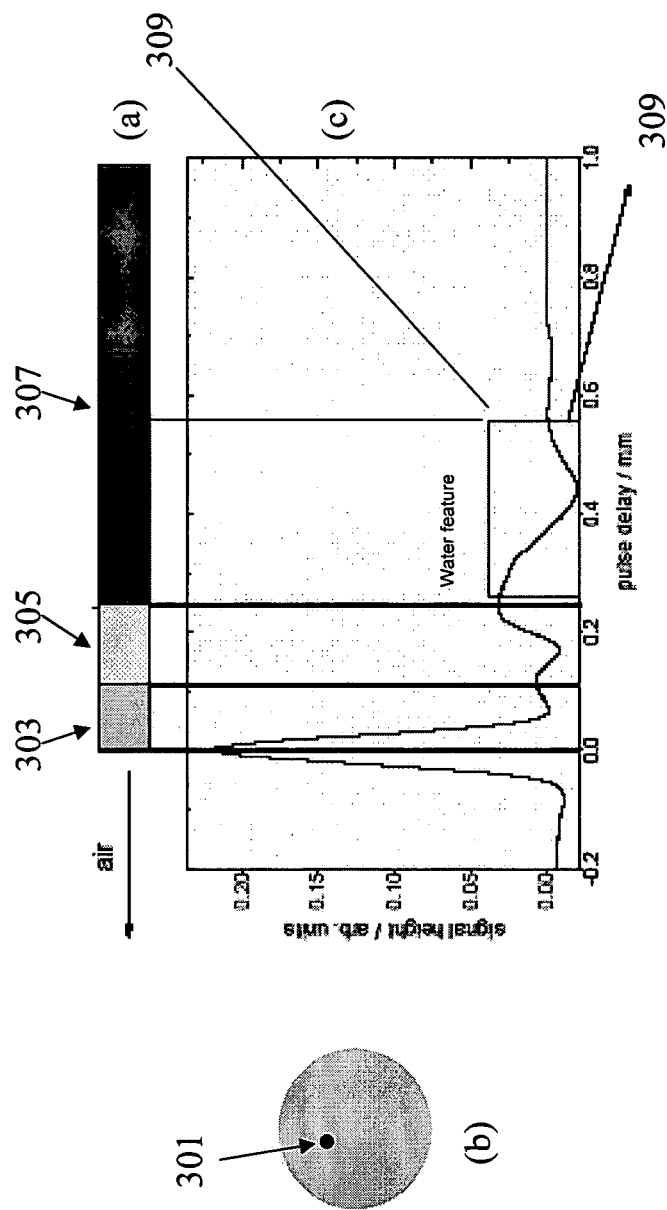
Figure 23:
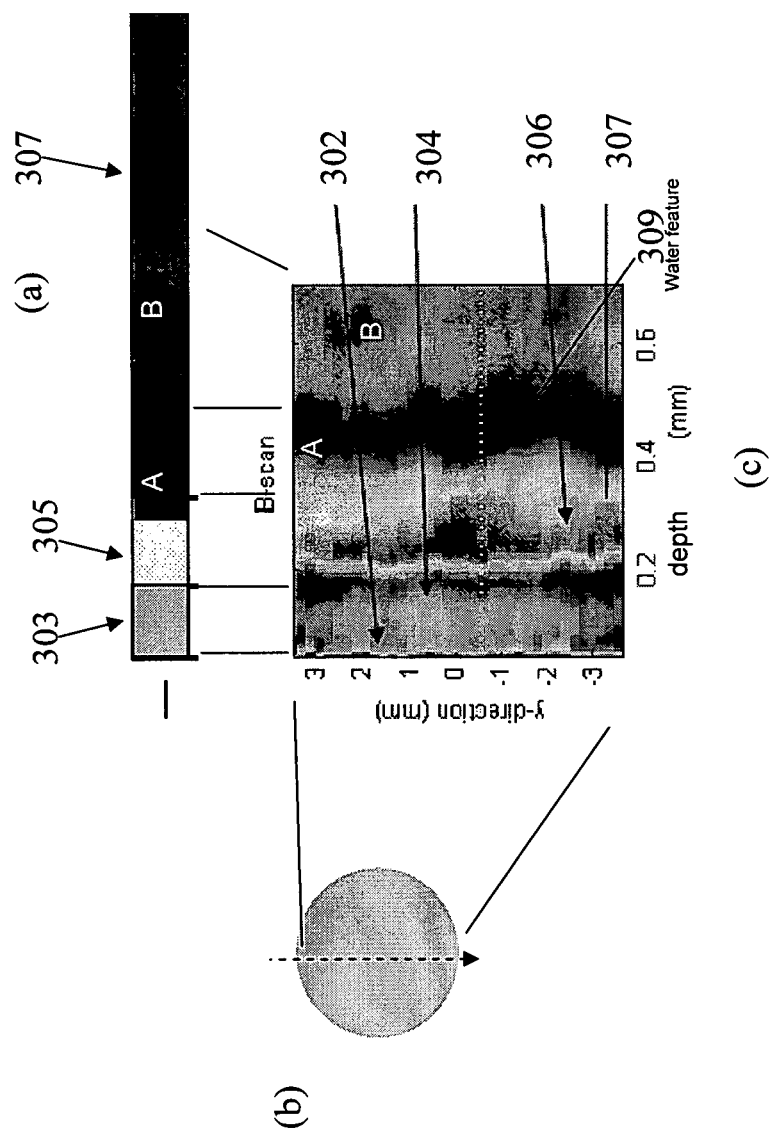

FIG. 23 shows a slight variation on the data of FIG. 22. Again, a cross-section through a tablet FIG. 13a is shown which is identical to that of FIG. 23. The tablet is shown in FIG. 23b which is again identical to that of FIG. 23b. However, in this case, data is obtained by performing a linear scan of the point 301 shown in FIG. 18b. A trace similar to that shown in FIG. 22c is obtained for each point along the scan. FIG. 23c is an image constructed from these traces shown in grey scale with dark regions corresponding to a low reflection signal and light regions corresponding to a higher reflection signal. The structure of the tablet is the same as that shown in FIG. 20a and the same reference numerals have been used. The water ingression is shown as dark band 309 on image FIG. 13c.

FIG. 24a is a schematic cross-section of a tablet showing an API layer 401 and a water layer 403. The water layer is due to contamination.

FIG. 24b is a terahertz cross-section of the tablet of FIG. 24a. The water layer 403 can be easily seen. Also, a defect in the API layer 405 can also be clearly seen in the terahertz image.

It should be noted that this technique can also be used to quantify the amount of water present in a table. In this mode, the amplitude, area or related parameter associated with the water feature in FIG. 22c (centred at 0.4 mm) can be used to quantify the amount of water available. Spectral information, related to a Fourier transform or short Fourier transform of this peak, can also be used.

In transmission mode, the entire pulse will pass through the tablet, and the amplitude in the time domain and/or spectral information can be used to determine water content from the amount of absorption. This is analogous to the spectral transmission measurements used to look at API identification and quantification on pharmaceutical tablets.

Figure 25:
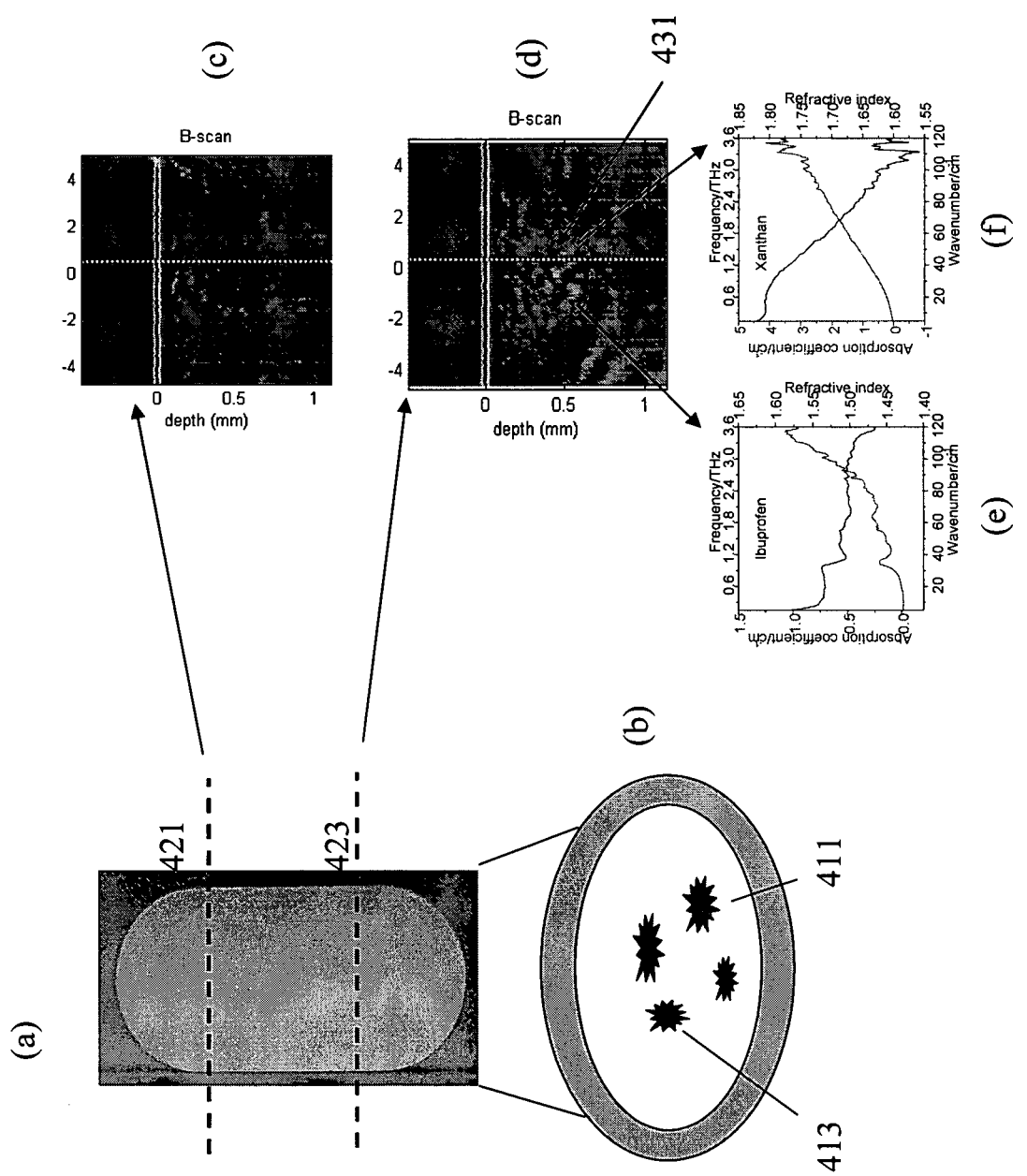

FIG. 25 schematically demonstrates how terahertz can be used to determine clumping of the excipient or the API. FIG. 25a is a visible image of a tablet. FIG. 25b is a schematic cross section of the tablet showing clumping of the API 411 and clumping of the excipient 413. Terahertz images of the type described previously are taken for two cross sections 421 and 423 across the tablet of FIG. 25a.

The cross-section 421 is shown in FIG. 25c and it can be seen that the image is fairly uniform and there is no aggregation seen. However, in the image of FIG. 25d which is taken for cross-section 423, aggregation is seen in area 431. The formation of a number of clumps can be easily seen.

It is difficult to determine which of these clumps are API and which are the excipient. In the particular example shown here, the excipient is Xanthan the THz spectra of which is shown in FIG. 25f and the API is Ibuprofen the terahertz spectra of which is shown in FIG. 25e. Terahertz spectra can easily be obtained by taking the time domain trace and converting it into the frequency domain. Performing this analysis in the regions clumps are seen will allow identification of the constituents of the clumps. It is also possible to look at changes in the refractive index or interface index due to the clumps, and correlate those with known changes due to APIs or excipient clumping in such matrices.

Terahertz radiation may also be used to determine the particle size of particles in a mixture in a tablet. Almost all pharmaceutical tablets are produced by compressing powder mixtures. By irradiating such a mixture with terahertz radiation, it is possible to obtain an extinction spectra. Extinction spectra is expressed by the formula:

$$\varepsilon(\nu) = -2\log_{10}\left(\int_{-\infty}^{\infty} E^{THz}_{samp}(t)e^{j2\pi\nu t}dt \bigg/ \int_{-\infty}^{\infty} E^{THz}_{ref}(t)e^{j2\pi\nu t}dt\right)$$

where $\nu$ is the frequency

The reference spectra is obtained by an empty powder cell.

FIG. 26a shows an extinction spectra recorded for powders. The extinction increases with frequency in the range of 0.5 to 3.0 terahertz. The extinction spectra can be modelled using the equation:

$$\epsilon(\nu) = B\nu^A$$

In this particular example, parameter A was found to have best fit value of 3.3+/−0.2 for all particles sizes studied. This indicates that the scatter-induced extinction increases as the 3.3 power of the frequency. Parameter B was found to increase as a third of the power of the particle size and this is shown in FIG. 26b. Theoretical calculations indicate that for particles of the sizes, the extinction is proportional to the sixth power of the particle size. However, the particle number density decreases as the particle size for the power of 3 because the PE mass in the cell is constant (300 milligrams) this explains that the overall extinction increases as the power to the 3 of the particle size in the range 50 to 200 µm.

Figure 27:
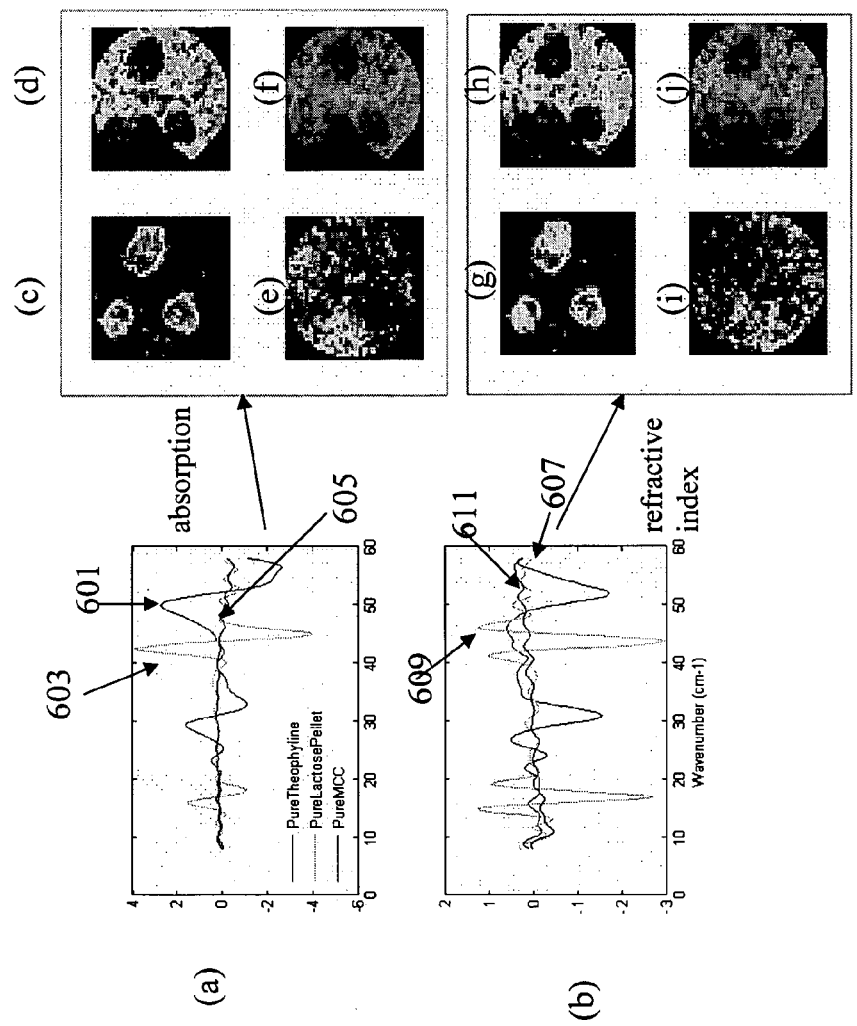

FIG. 27 relates to a spectral mapping technique known as cosine correlation mapping or spectral angle mapping. FIG. 27a shows three spectra of three different components mainly, pure theophyline 601, pure lactose 603 and pure MCC 605. Terahertz radiation can be used to show how these components are distributed within a tablet. In this particular example, a tablet is constructed comprising an MCC and lactose mixture with three areas replaced by three smaller theophyline pellets.

Terahertz refractive index data for the tablet is expressed in terms of a pixel vector: $\vec{p} = [p_1, p_2, \ldots, p_n]$ where $p_i$ is the absorption coefficient (or refractive index) measured at wavelength $\lambda_i$ for the specific pixel.

For chemical mapping purpose, we will need the terahertz spectrum of the pure chemical under investigation. We call it as the target vector A target vector ($\vec{t} = [t_1, t_2, \ldots, t_n]$) where $t_i$ is the absorption coefficient (or refractive index) measured at wavelength $\lambda_i$ for the pure chemical is then generated for the chemical of interest using the data shown in FIG. 27a.

The pixel vector and target vector are then compared in order to produce maps of the types shown in FIGS. 27c to f and 27g to j. FIGS. 27c, d and e are derived from cosine correlation analysis where the quantity α is plotted:

$$\alpha = \arccos\left(\frac{\sum_{i=1}^{n} t_i p_i}{\sqrt{\sum_{i=1}^{n} t_i^2} \sqrt{\sum_{i=1}^{n} p_i^2}}\right)$$

By processing the above equation, the smaller the angle α the greater similarity between the pixel and target spectra.

FIG. 27c shows results for this analysis where the target vector is theophyline so map c can be thought of as a chemical map showing the distribution of theophyline within the pellet. Map 27d is constructed by using a target vector of lactose and map 3 using the target vector of MCC. The map of 27f is generated by combining the three maps c, d and e and can only really usefully be represented via a full colour plot where the grey scale maps of c, d and e are each assigned a different colour.

FIG. 27b shows three terahertz spectra again for pure theophyline 607, pure lactose 609 and pure MCC 611 but this time the spectra is expressed in terms of refractive index and opposed to absorption.

The target vector for these three compounds is expressed in terms of refractive index as opposed to absorption and the measured pixel vector for the tablet is also expressed in terms of refractive index as opposed to absorption. Again, three chemical maps are derived for each of the target vectors. Map 27g is for a target vector of pure theophyline, map 27h is for a target vector of pure lactose and map 27i is for a target vector of pure MCC. Map 27j is a combination of the three maps 27g, h and i and again can be much more clearly understood if it is printed in full colour.

α has a value between 0 and π/2. In order to plot it so it has values between 0 and 1, it may be plotted as:

$$MSAS = \frac{2\alpha}{\pi}$$

Alternatively, the cosine of α can be plotted to also obtain values between 0 and 1.

Cosine correlation mapping or spectral angle are just one of the ways of comparing a target vector and a pixel vector in order to determine a chemical distribution within a sample.

Spectral distance mapping is a technique where $Ed_{orig}$ (Euclidean distance) is determined $$Ed_{orig} = \sqrt{\sum_{i=1}^{n}(t_i - p_i)^2}$$

This value may be scaled to be between 0 and 1 by:

$$Ed = (Ed_{orig} - m)/(M - m)$$

where m and M are the minima and maximum of $Ed_{orig}$ values respectively.

Another technique is so called spectral correlation mapping where the Pearson statistical correlation is used as a comparison measure. This is known as:

$$\rho = \frac{1}{1-n}\left(\frac{\sum_{i=1}^{n}(t_i - \mu_{ti})(p_i - \mu_{pi})}{\sigma_t \sigma_p}\right)$$

where $\mu_p$ and $\sigma_p$ are the mean and standard deviation of the pixel vector respectively and $\mu_t$ and $\sigma_t$ are the mean and standard deviation of the target vector respectively.

The above two techniques can be combined in order to show spectral similarity mapping. This is determined by the equation:

$$SSV = \sqrt{Ed^2 + (1-\rho)^2}$$

Other chemical mapping techniques which use partial squares analysis and multi-variable analysis using the absorption and/or refractive index are found to be particularly successful.

The techniques described above may be combined with any of the techniques described in the applicant's earlier patent applications and specifically GB 2 397 207, GB 2 405 466 and GB 2 405 200.

What is claimed is:

1. A method of determining dissolution characteristics of a tablet, the method comprising:
   irradiating a tablet with radiation having at least one frequency in the range from 40 GHz to 100 THz;
   detecting radiation which has been transmitted through or reflected by the tablet;
   determining an indication of the density of a coating layer of the tablet from the detected radiation; and
   determining information about the dissolution characteristics of the tablet from the indication of the density.

2. A method according to claim 1, wherein the indication of the density is the thickness of the tablet coating.

3. A method according to claim 2, wherein the information about the dissolution characteristics is determined by using a negative correlation between the coating thickness or time of flight of radiation through the coating and the time which dissolution takes.

4. A method according to claim 1, wherein the indication of the density is the time of flight of the radiation through the tablet coating.

5. A method according to claim 1, further comprising measuring the weight of the tablet coating.

6. A method according to claim 1, wherein the indication of the density is the refractive index of the tablet coating.

7. A method according to claim 6, wherein the refractive index is determined from the maximum signal strength of the radiation reflected by the tablet.

8. A method according to claim 1, wherein the indication of the density is the size of the signal reflected from the interface between the coating and the core of the tablet.

9. A method according to claim 1, wherein the indication of the density is the size of the signal reflected from the external surface of the tablet.

10. A method according to claim 1, wherein the indication of the density is the size of the signal reflected from the interface between the coating and the core divided by the size of the signal reflected from the external surface of the tablet.

11. A method according to claim 1, wherein the information about the dissolution characteristics is determined by using a positive correlation between the density and the time which dissolution takes.

12. A method according to claim 1, wherein the dissolution characteristics are defined by dissolution parameters selected from: the mean dissolution time; the dissolution rate constant and the dissolution at specified times.

13. A method according to claim 1, further comprising measuring the indication of the density for a plurality of points on said tablet.

14. A method according to claim 13, wherein the indication of the density is measured on the two main opposing surfaces of the tablet and the central band.

15. A method according to claim 1, wherein the indication of the density is measured on the central band.

16. A method according to claim 1, wherein the tablet is a sustained release tablet.

17. A method of determining dissolution characteristics of a tablet, the method comprising:
   irradiating a tablet with radiation having at least one frequency in the range from 40 GHz to 100 THz; detecting radiation which has been reflected by the tablet; determining an indication of the density of a coating layer of the tablet from a maximum signal strength of the radiation reflected by the tablet; and determining information about the dissolution characteristics of the tablet from the indication of the density wherein a measurement of the dissolution characteristics is obtainable from the maximum signal strength reflected from a single point on the tablet coating.

18. A method according to claim 17, wherein the information about the dissolution characteristics is determined by using a positive correlation between at least one dissolution parameter and the maximum signal strength.

19. A method according to claim 18, wherein the dissolution parameter is selected from: the mean dissolution time; the dissolution rate constant and the dissolution at specified times.

20. A method of determining if a tablet is of sufficient quality, said method comprising:
   irradiating a tablet with pulsed radiation having at least one frequency in the range from 40 GHz to 100 THz;

detecting radiation which has been transmitted through or reflected by the tablet;

determining an indication of the density of a coating layer of the tablet from the detected radiation; and determining if said tablet is of sufficient quality by comparing the density of the tablet with a pre-determined reference value and rejecting said tablet the density of the coating layer is lower than said reference value.

21. A method according to claim 20, wherein determining a parameter indicative of an indication of the density of the tablet coating comprises determining the weight of the coating and dividing it by the amplitude of the reflected THz signal.

22. An apparatus for performing dissolution analysis on a tablet, comprising:

a source for irradiating a tablet with radiation having at least one frequency in the range from 40 GHz to 100 THz;

a detector for detecting radiation which has been transmitted through or reflected by the tablet;

a processor for determining an indication of the density of a coating layer of the tablet from the detected radiation; and a processor for determining information about the dissolution characteristics of the tablet from said indication of the density.

23. An apparatus according to claim 22, wherein said source is a source of pulsed radiation.

24. An apparatus according to claim 22, wherein the processor for determining a parameter indicative of the density of a coating layer of the tablet comprised means for determining the time of flight of radiation through said coating layer.

25. An apparatus according to claim 22, wherein the processor for determining an indication of the density of the coating layer of the tablet comprises means for determining the strength of the reflected radiation signal.

* * * * *